(12) United States Patent
Bergquist et al.

(10) Patent No.: US 12,186,196 B2
(45) Date of Patent: *Jan. 7, 2025

(54) ELBOW ARTHROPLASTY APPARATUS, SYSTEM, AND METHOD

(71) Applicant: Acumed LLC, Hillsboro, OR (US)

(72) Inventors: Jeff Bergquist, Portland, OR (US); Caleb Martin, Tualatin, OR (US); Mark Sommers, Beaverton, OR (US); Bryon Morse, Lake Oswego, OR (US)

(73) Assignee: Acumed LLC, Hillsboro, OR (US)

( * ) Notice: Subject to any disclaimer, the term of this patent is extended or adjusted under 35 U.S.C. 154(b) by 664 days.

This patent is subject to a terminal disclaimer.

(21) Appl. No.: 17/406,831

(22) Filed: Aug. 19, 2021

(65) Prior Publication Data

US 2021/0378830 A1 Dec. 9, 2021

Related U.S. Application Data

(63) Continuation of application No. 15/016,013, filed on Feb. 4, 2016, now Pat. No. 11,096,786.

(60) Provisional application No. 62/111,963, filed on Feb. 4, 2015.

(51) Int. Cl.
*A61F 2/38* (2006.01)
*A61F 2/30* (2006.01)

(52) U.S. Cl.
CPC ...... *A61F 2/3804* (2013.01); *A61F 2002/305* (2013.01); *A61F 2002/30515* (2013.01); *A61F 2002/30624* (2013.01); *A61F 2002/30649* (2013.01); *A61F 2002/30784* (2013.01); *A61F 2002/3813* (2013.01); *A61F 2002/3822* (2013.01); *A61F 2002/3831* (2013.01)

(58) Field of Classification Search
CPC ............ A61F 2/3804; A61F 2002/2896; A61F 2002/3809; A61F 2002/3813; A61F 2002/3818; A61F 2002/3822; A61F 2002/3827; A61F 2002/3831; A61F 2/38; A61F 2002/13; A61F 2002/22; A61F 2002/31

See application file for complete search history.

(56) References Cited

U.S. PATENT DOCUMENTS

2012/0053697 A1* 3/2012 Palmer .................. A61F 2/3804
623/20.12
2013/0345818 A1* 12/2013 Wagner ................ A61F 2/3804
623/20.12

* cited by examiner

*Primary Examiner* — Christopher D. Prone
(74) *Attorney, Agent, or Firm* — K&L Gates LLP

(57) ABSTRACT

The present disclosure generally relates to an elbow arthoplasty prosthesis that includes an ulnar component, a humeral component, one or more articulation liners, and a retention trap. The ulnar component includes a spherical bearing head that can be inserted into the humeral component in a number of orientations. The articulation liners and the retention trap are operatively engaged to the humeral component to retain the ulnar component within a humeral socket. The present disclosure also relates to methods of assembling and implanting the prosthetic device.

18 Claims, 28 Drawing Sheets

ELBOW ARTHROPLASTY APPARATUS, SYSTEM, AND METHOD

RELATED APPLICATIONS

This application is a continuation of U.S. application Ser. No. 15/016,013, filed Feb. 4, 2016, which issued as U.S. Pat. No. 11,096,786 on Aug. 24, 2021, which claims priority to U.S. Provisional Application No. 62/111,963, entitled "Elbow Arthroplasty Apparatus, System, And Method," filed on Feb. 4, 2015, each of which is incorporated herein by reference in its entirety, including any appendices.

TECHNICAL FIELD

Aspects of the present disclosure relate to joint apparatuses and in particular apparatus, systems, and methods for elbow arthroplasty.

BACKGROUND

Joint arthroplasty is a mechanism commonly used for relieving pain and restoring function to patients suffering from arthritis and other destructive joint problems, in joints such as the elbow. Advancements in implant designs and surgical techniques have made elbow arthroplasty a satisfactory treatment for arthritic disorders.

SUMMARY

The present disclosure generally relates to an elbow arthoplasty apparatus and system that may be used in elbow replacement. In various embodiment, that disclosed system includes an elbow prosthesis and/or implant device and related instruments and components that may be used to implant the elbow prosthesis.

In one embodiment, an elbow arthoplasty apparatus an ulnar component, a humeral component, at least one articulation liner, and a retention trap. The ulnar component further includes a spherical bearing head having one or more projection ears extending away from the bearing head along a central transverse axis of the bearing head. The bearing head is operatively engaged to an ulnar stem extending away from the bearing head in a direction generally perpendicular to the transverse axis.

The humeral component includes a yoke, and a pair of opposing yoke branches extending from the yoke. An interior surface of each yoke branch is concave. An exterior surface of each yoke branch is concave. The yoke branches define a spherical socket to retain the bearing head when disposed in the socket. The humeral component also includes a stem extending from the yoke opposite the pair of opposing yoke branches.

The at least one articulation liner is operatively engaged to the interior surface of at least one of the pair of yoke branches. The at least one articulation liner is also disposed within the spherical socket between the at least one yolk branch and the spherical bearing head. The retention trap is operatively engaged to the pair of opposing yoke branches, the at least one articulation liner, the bearing head and the one or more projection ear.

In one embodiment, a method of implanting the elbow arthoplasty apparatus includes obtaining the elbow prosthesis. The elbow prosthesis includes an ulnar component including a bearing end and an ulnar stem. The ulnar stem is coupled to the bearing end and extends away from the bearing end. The elbow prosthesis also includes a humeral component including a holder end and a humeral stem. The humeral stem extends away from the holder end. The elbow prosthesis further includes at least one bearing liner coupled to the holder end. The bearing end is configured to be coupled within the holder end to articulate against the at least one bearing liner.

The method includes making an incision in the patient, determining the proper size for the ulnar component and the humeral component, and preparing an ulna and a humerus of the patient. The method also includes securing the humeral component into the humerus of the patient, attaching the ulnar component to the humeral component, securing the ulnar component into the ulna of the patient, and closing the incision in the patient.

In one aspect, a method of implanting an elbow arthoplasty apparatus may also include inserting the bearing end of the ulnar component into the holder end of the humeral component adjacent to the at least one bearing liner. A retention trap is inserted into the holder end. The method may also include securing the at least one bearing liner to an inner surface of the holder end by rotating the at least one bearing within the humeral component to engage a locking flange of the bearing liner with the a locking shoulder of the humeral component. This may be accomplished by rotating the retention trap and the at least one bearing liner relative to the humeral component to lock the retention trap and the at least one bearing liner to the humeral component.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

DETAILED DESCRIPTION

Aspects of the present disclosure involve an elbow arthoplasty apparatus and system that may be used in elbow replacement. In one aspect, the disclosed system includes an elbow prosthesis and/or implant device and related instruments and components that may be used to implant the elbow prosthesis. In another aspect, the disclosed prosthetic device is a total elbow arthroplasty device designed to restore range of motion to the elbow while replacing the native bony and articulating anatomy of the ulnohumeral interface.

The elbow arthoplasty apparatus disclosed herein includes various embodiments of an implantable prosthetic device that generally comprises a humeral component, an ulnar component, one or more articulation bearing inserts or liners, and a retention trap, all assembled to form a general a ball and socket type configuration. The humeral component and ulnar component are articulable relative to one another, while the various liners and retention devices associated with the ball- and socket connection to permit easier assembly or replacement of the prosthesis. In various embodiments, the prosthetic device 10 is provided in a variety of sizes and may be configured for implantation into a variety of patients such as pediatric patients or adult patients.

Figure 7:
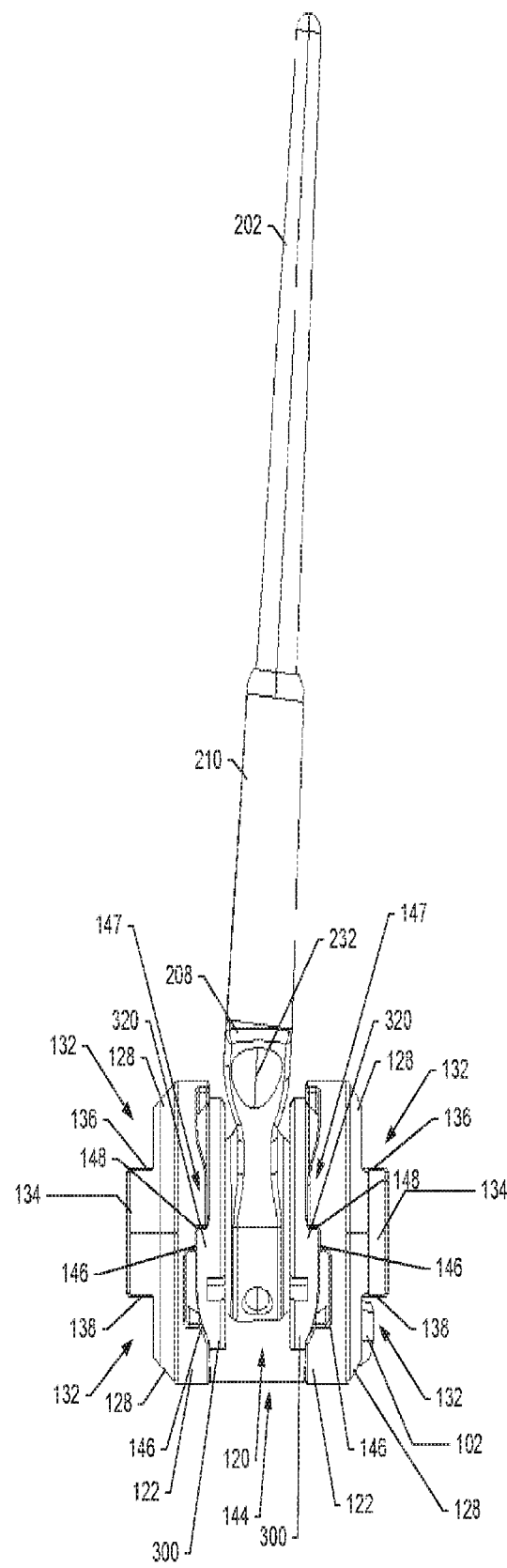
FIG. 7 is a bottom perspective view of the elbow implant device of FIG. 1 without a retention trap.
Figure 8:
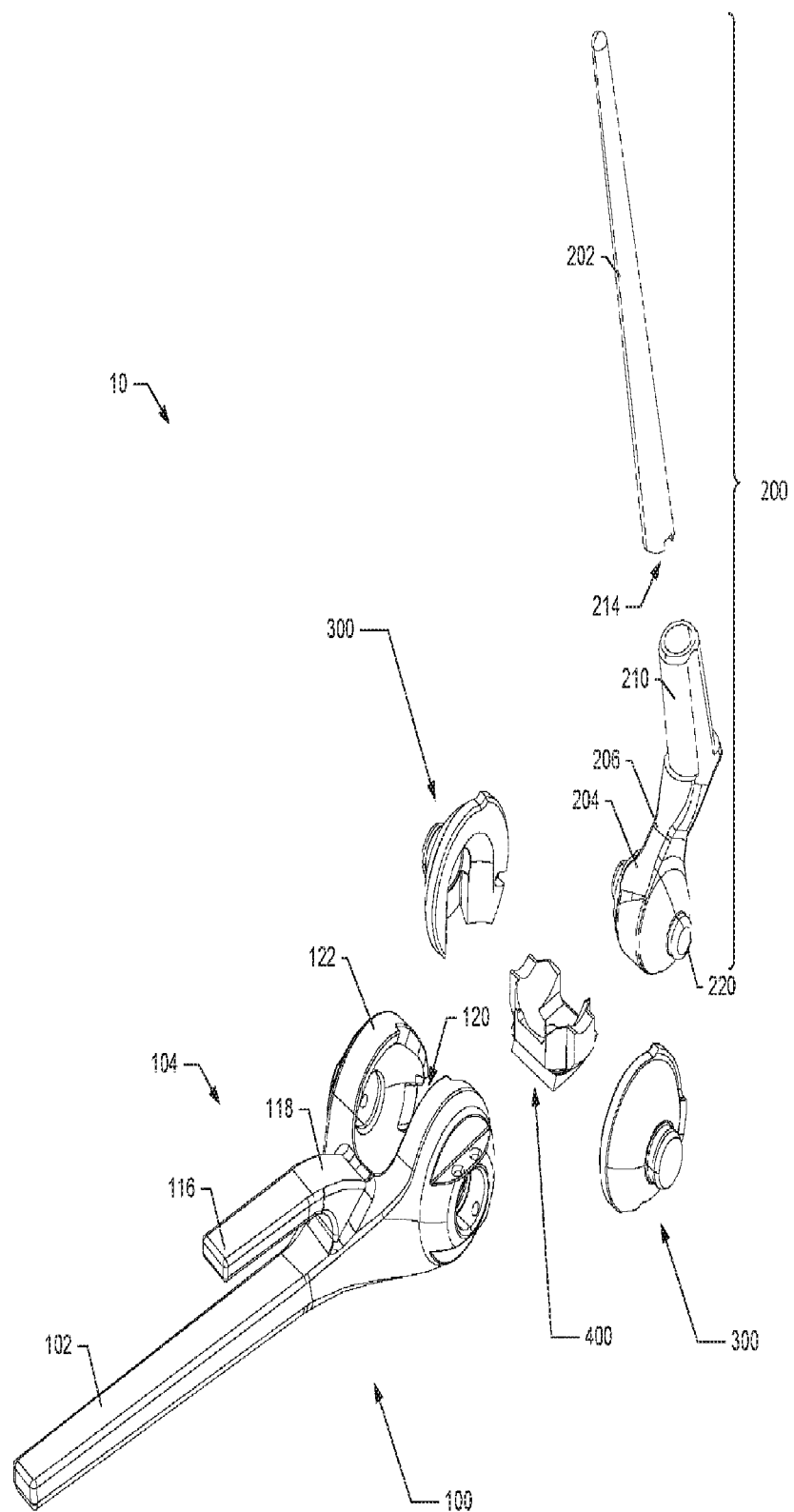
FIG. 8 is an exploded view of the elbow implant device of FIG. 1 in an unassembled configuration.

Referring to FIGS. 1-8, the elbow prosthesis or prosthetic device 10 comprises the humeral component 100 and the ulnar component 200. The elbow prosthesis 10 further includes one or more bearing liner, referred to herein as an articulation liner 300 and a retention trap 400, as shown in FIG. 8.

The Humeral Component

In various embodiments, the humeral component 100 includes an elongated humeral stem 102, an elongated humeral flange 104, and a holder end, referred to herein as humeral socket 106. In one aspect, the humeral component 100 is composed of a bio-compatible metal or metal alloy is designed for cemented fixation within the humeral canal of a patient. By way of example, the humeral component 100 may be composed of Grade 5 or Grade 23 titanium, such as that having the formula Ti-6Al-4V. Other suitable metals and metal alloys including other titanium alloys may also be used. Additionally, various other biocompatible materials including other metals, and polymers, or combinations thereof may be used for the humeral component 100, as well as any other portion of the prosthetic device 10.

Figure 5:
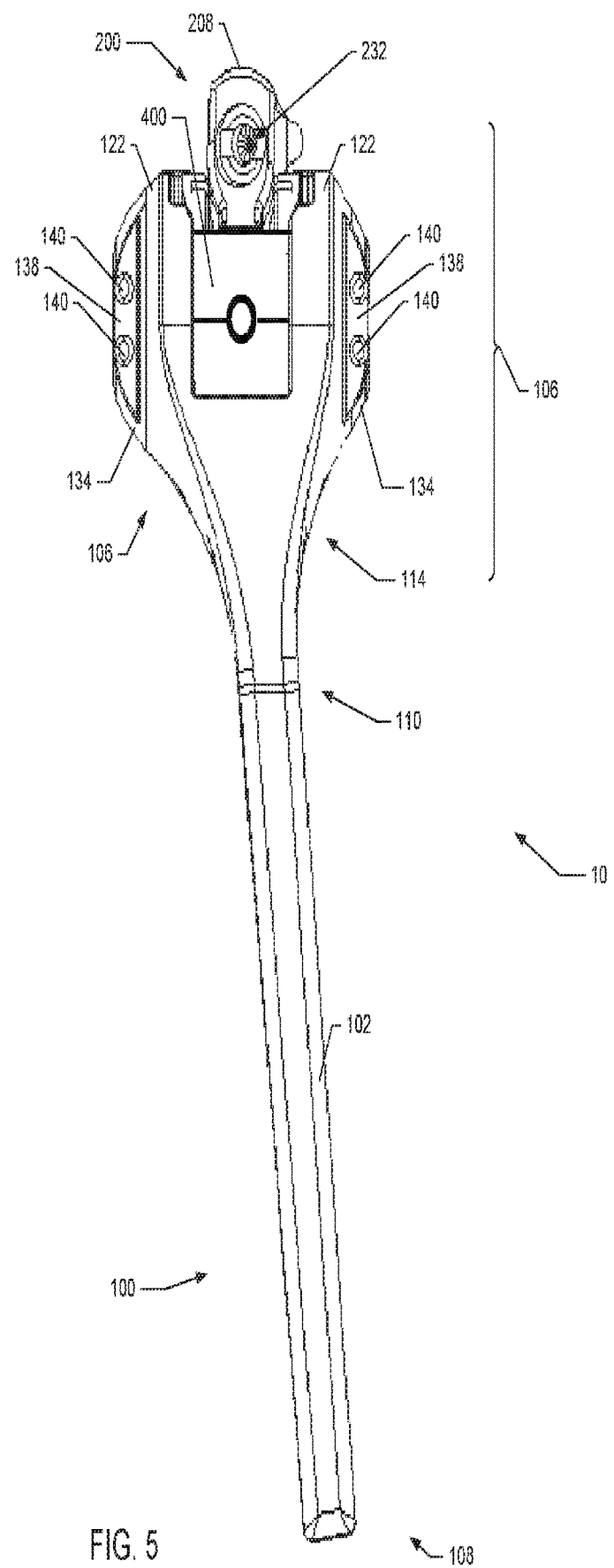
FIG. 5 is a rear orthographic view of the elbow implant device of FIG. 1.
Figure 6:
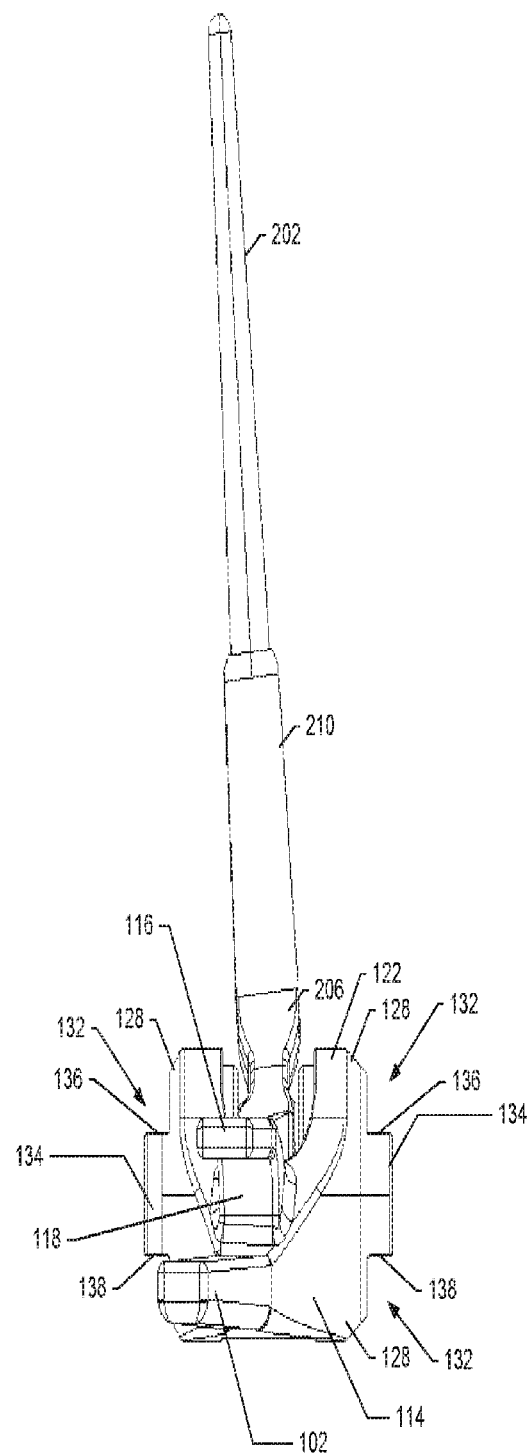
FIG. 6 is a top perspective view of the elbow implant device of FIG. 1.

The humeral stem 102 includes a proximal end 108 that extends proximally from the humeral socket 106 and a distal end 110 that transitions into the humeral socket 106. The proximal end 108 of the humeral stem 102 has a generally rectangular cross-section and is dimensioned for implantation in the humerus. In one aspect, the rectangular cross-section of the humeral stem 102 provides rotational stability. Similarly, the humeral flange 106 contacts the anterior surface of the distal humerus after implantation. The rectangular cross-section of the humeral flange 106 thus maximizes the surface contact area with the anterior surface of the humerus. The width of the proximal end 108 of the humeral stem 102 increases along the length of the stem to a width of as it transitions into the distal end 110 that is proximal to the humeral socket 106, as shown in FIG. 5. The dimensions and ratio of the taper along the length of the stem may depend upon the size of the device implanted.

Figure 1:
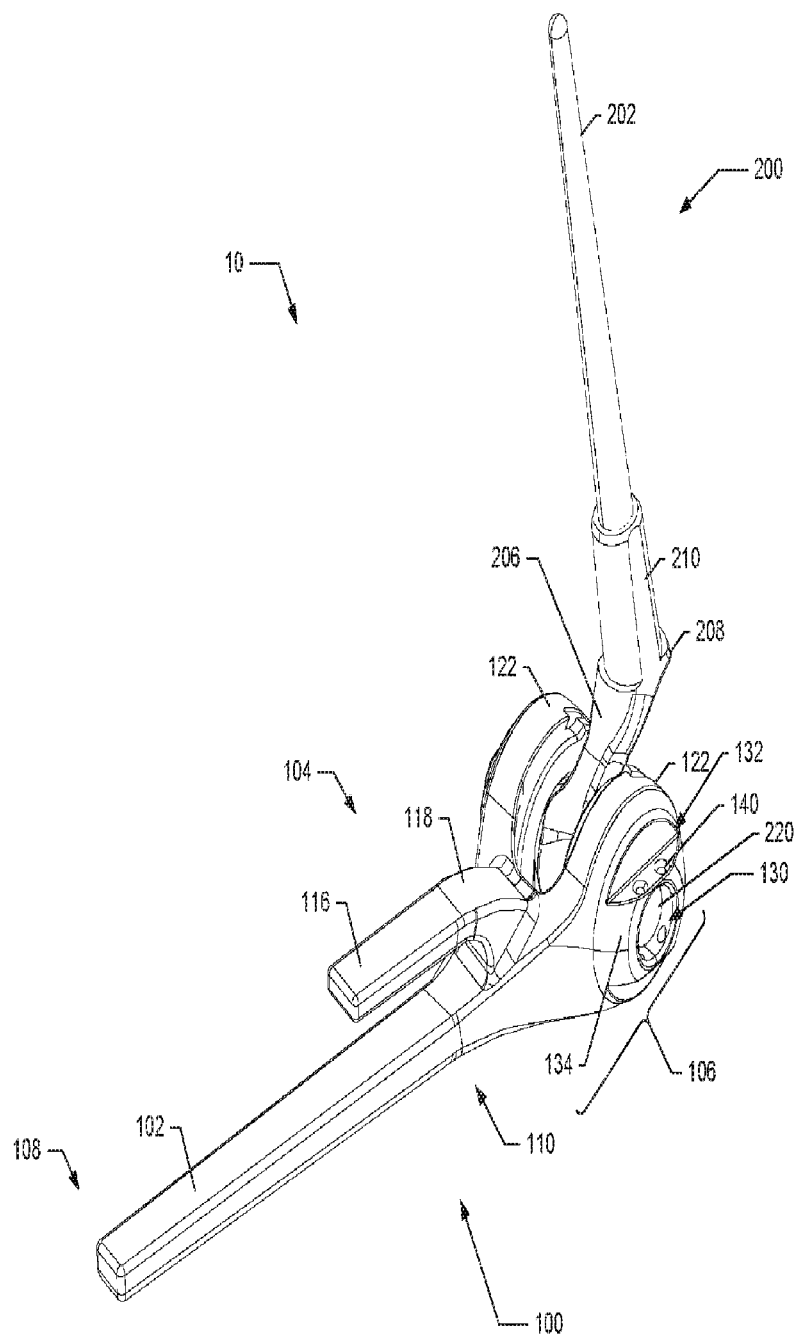
FIG. 1 is an isometric view of an elbow implant device in a fully assembled configuration.
Figure 2:
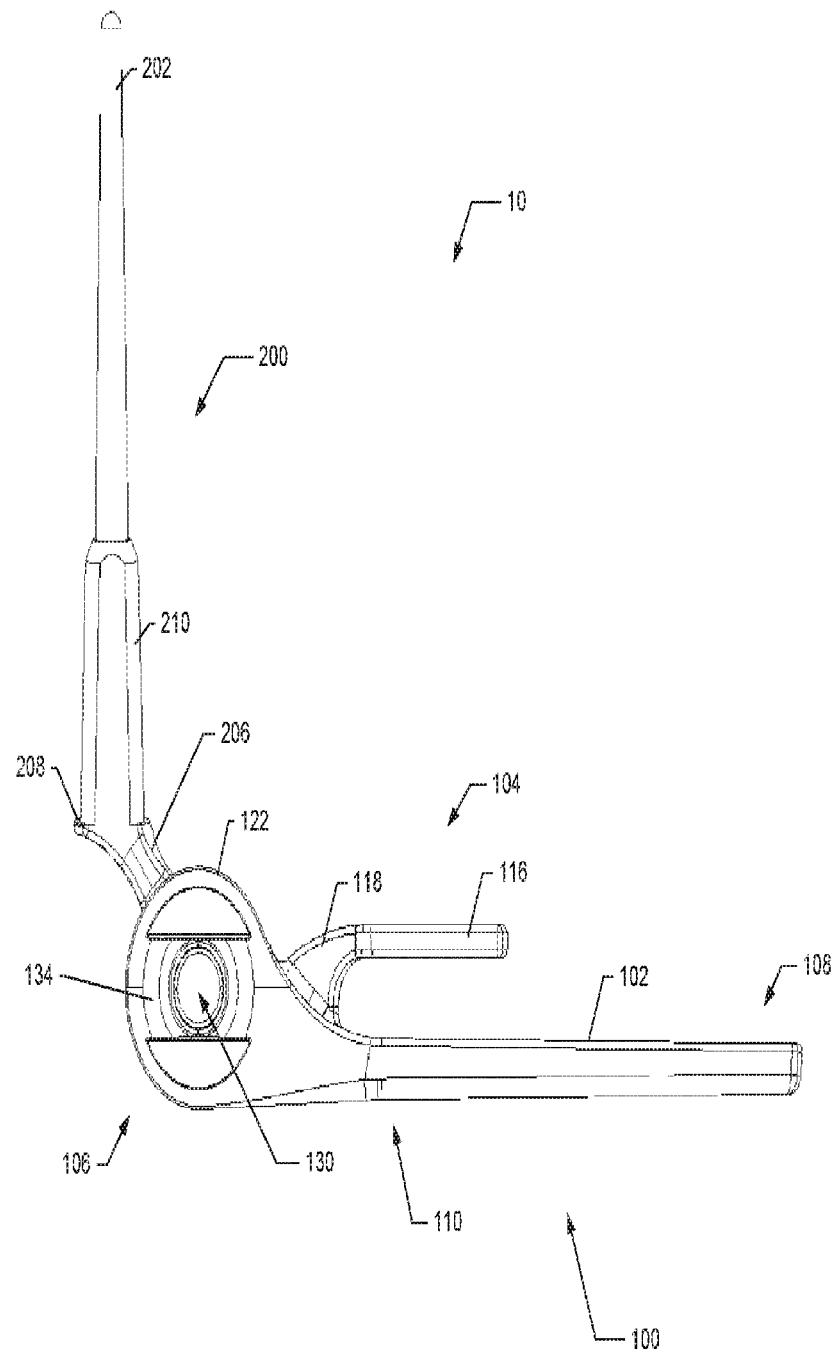
FIG. 2 is a left side elevation of the elbow implant device of FIG. 1.
Figure 3:
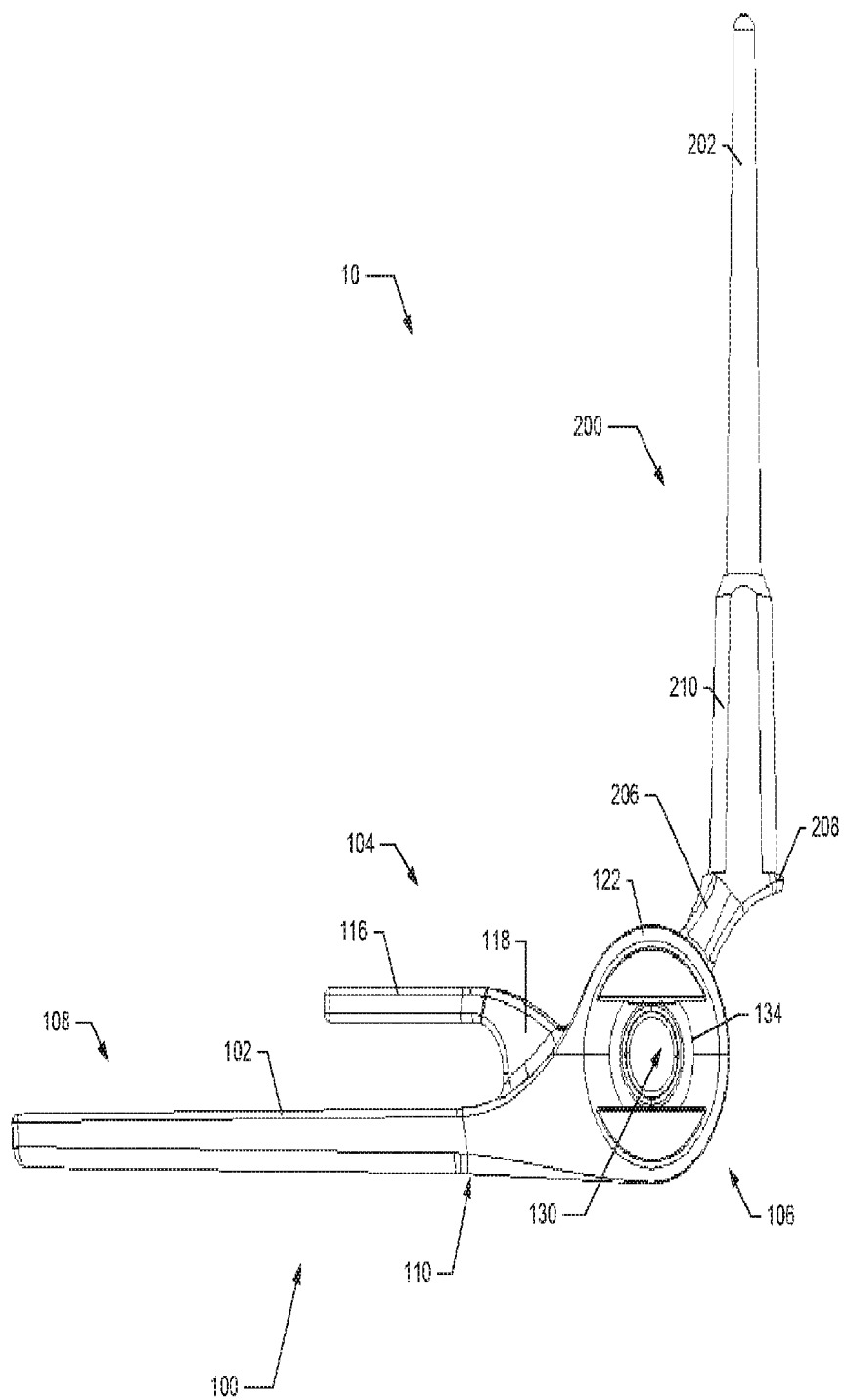
FIG. 3 is a right side elevation of the elbow implant device of FIG. 1.
Figure 4:
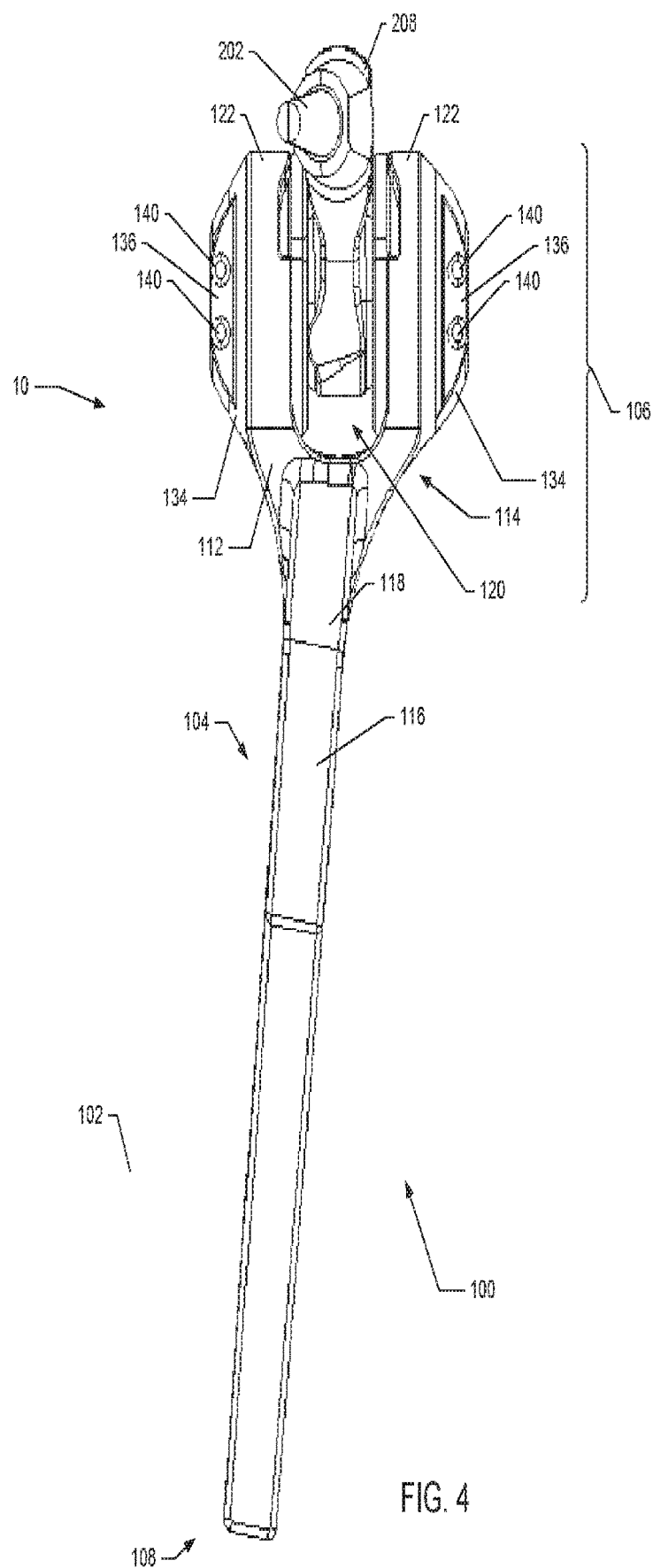
FIG. 4 is a front orthographic view of the elbow implant device of FIG. 1.

The humeral flange 104 extends proximally from an anterior surface 112 of a humeral socket yoke 114 and extends towards the proximal end 108 of the humeral stem 102. The humeral flange 104 extends in a plane substantially parallel to the humeral stem 102. As shown in FIGS. 1-3, 8, 9, 11, and 12, the humeral flange 104 includes a flange extension 116 and a flange base 118. The flange base 118 has the generally the same width as the flange extension 116. As shown in FIG. 3, the flange base 118 as a general arced configuration and tapers from a first thickness where it contacts the yoke 114 to a thickness that is substantially equal to the thickness of the humeral flange 104. In one aspect, the anterior humeral flange 104 provides support and rotational stability against torsional and posterior directed loads on the prosthesis 10.

As generally shown in FIGS. 1 and 8-10, the humeral socket 106 defines a cavity 120 which holds and retains the articulation liners 300, the ulnar component 200, and the retention trap 400 once the prosthesis 10 is fully assembled. In various embodiments, the humeral socket yoke 114 forks into two substantially parallel yoke branches 122. The humeral socket 106 receives and retains a ulnar bearing end, also referred to herein as bearing head 204 in a manner that permits articulation of the ulnar component 200 relative to the humeral component 100.

Figure 12:
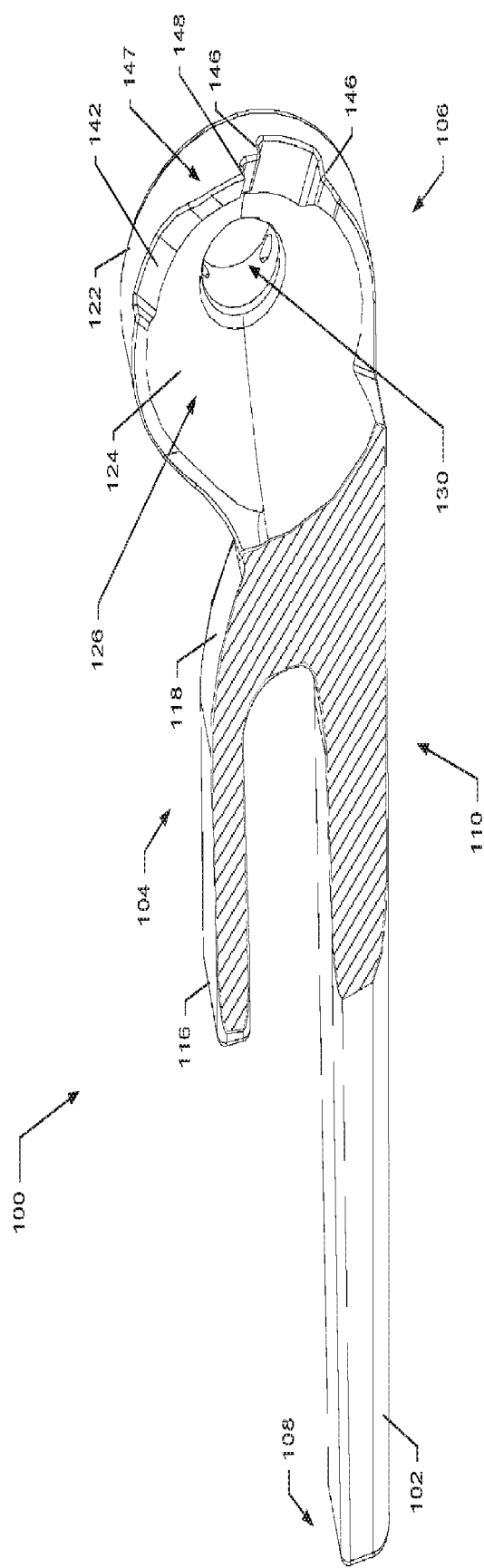
FIG. 12 is an isometric half-section view of the humeral component of the elbow implant device of FIG. 9.

Referring now to FIGS. 8-10 and 12, in one embodiment, the interior surface 126 of each yoke branch 122 is generally concave and define hemispherical recess 126, respectively, as shown in FIG. 12, that together define the cavity 120. Similarly, the exterior surfaces of each yoke branch defines a generally convex hemispherical surface 128. Each of the yoke branches 122 further includes a bearing bore 130, co-axially aligned with the pole of each hemispherical recess 126 and extending medially or laterally from the interior surface 126 to the exterior surface 128 of the branch.

In one embodiment, as shown in FIGS. 1, 6, 7, and 10, the exterior surface each of the yoke branches 122 are further defined by cutouts 132 that further a ridge 134 in a plane substantially parallel to the humeral stem 102. Each ridge 134 includes an anterior sidewall 136 and posterior sidewall 138. In this embodiment, the anterior sidewall 136, the posterior sidewall 138, or both further optionally include one or more suture bores 140 extending from the exterior of the respective sidewall 136 and/or 138 to the interior surface of the bearing bore 130. The suture bores 140 allow for the repair of soft tissue adjacent to the humeral component 100, the attachment of the prosthesis 10 to adjacent soft tissue, the attachment of the prosthesis 10 to the humeral condyles, or combinations thereof.

Figure 9:
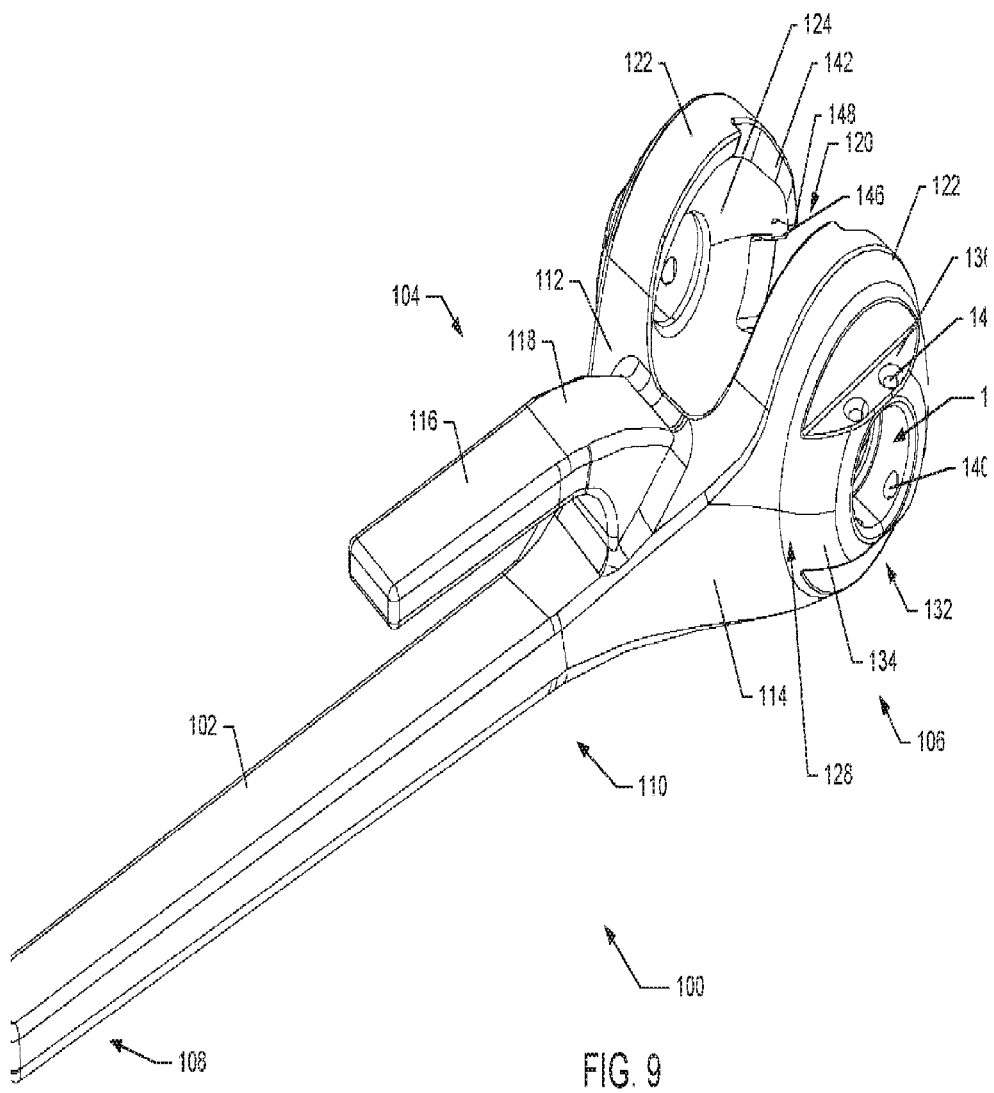
FIG. 9 is an isometric view of the humeral component of the elbow implant device of FIG. 8.
Figure 10:
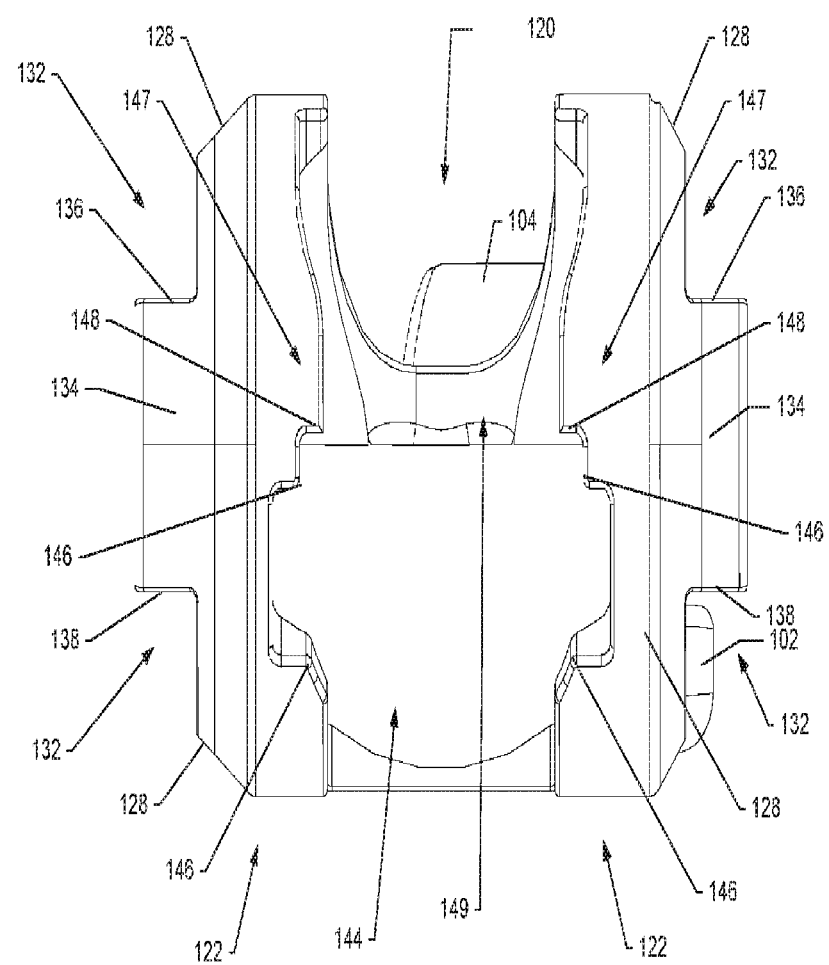
FIG. 10 is a bottom perspective view of the humeral component of the elbow implant device of FIG. 9.
Figure 11:
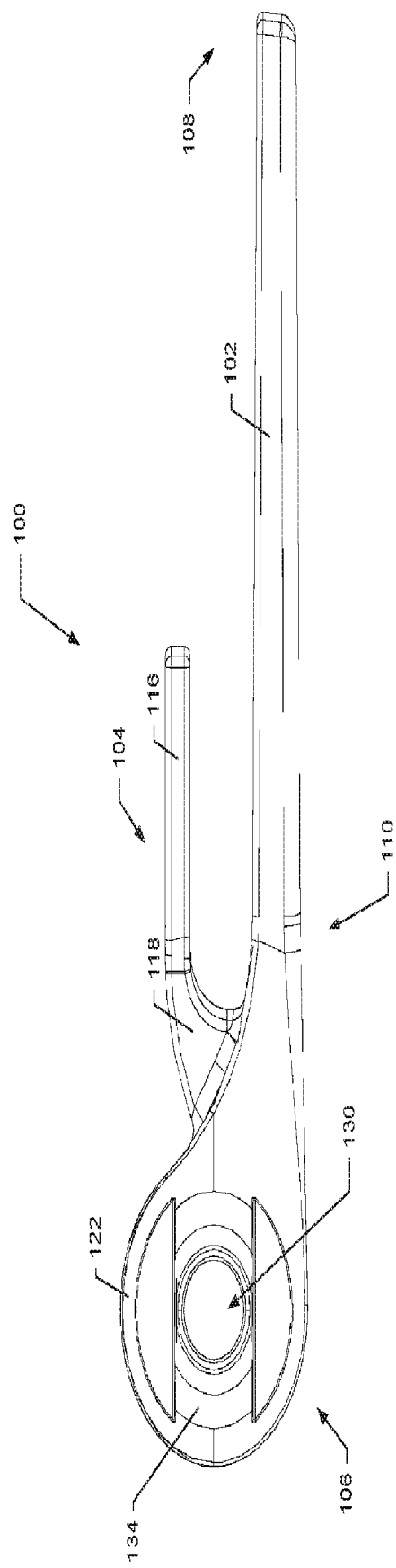
FIG. 11 is a left side elevation of the humeral component of the elbow implant device of FIG. 9.

As shown in FIGS. 9 and 12, the interior edges 142 of the yoke branches 122 define a slot 144 for receiving the ulnar component 200, the articulation liners 300, and the retention trap 400. The slot 144 further comprises a number of trap shoulders 146 to engage the retention trap 400, as well as a lock shoulder 148 to mechanically engage a flange 320 on the articulation liners 300, as shown in FIG. 7. The slot 144 further includes a narrowed or throttled region 149 that is formed by opposing tapered portions 147 of the interior edge 142 of the yoke branches 122, as shown in FIGS. 7, 10, and 12.

The Ulnar Component

Figure 15:
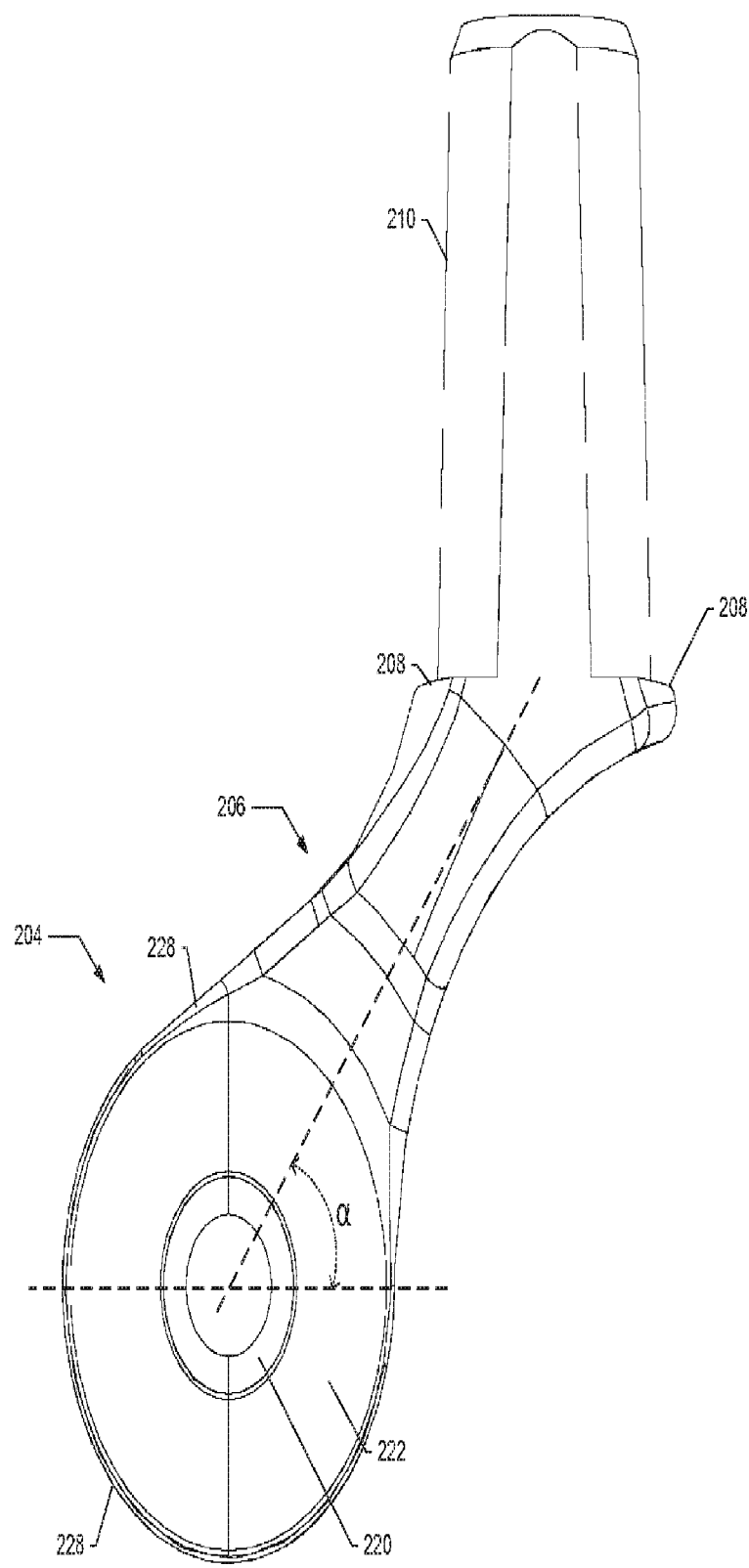
FIG. 15 is a right side elevation view of the bearing head, neck, and stem receptacle of the ulnar component of the elbow implant device of FIG. 13.
Figure 17:
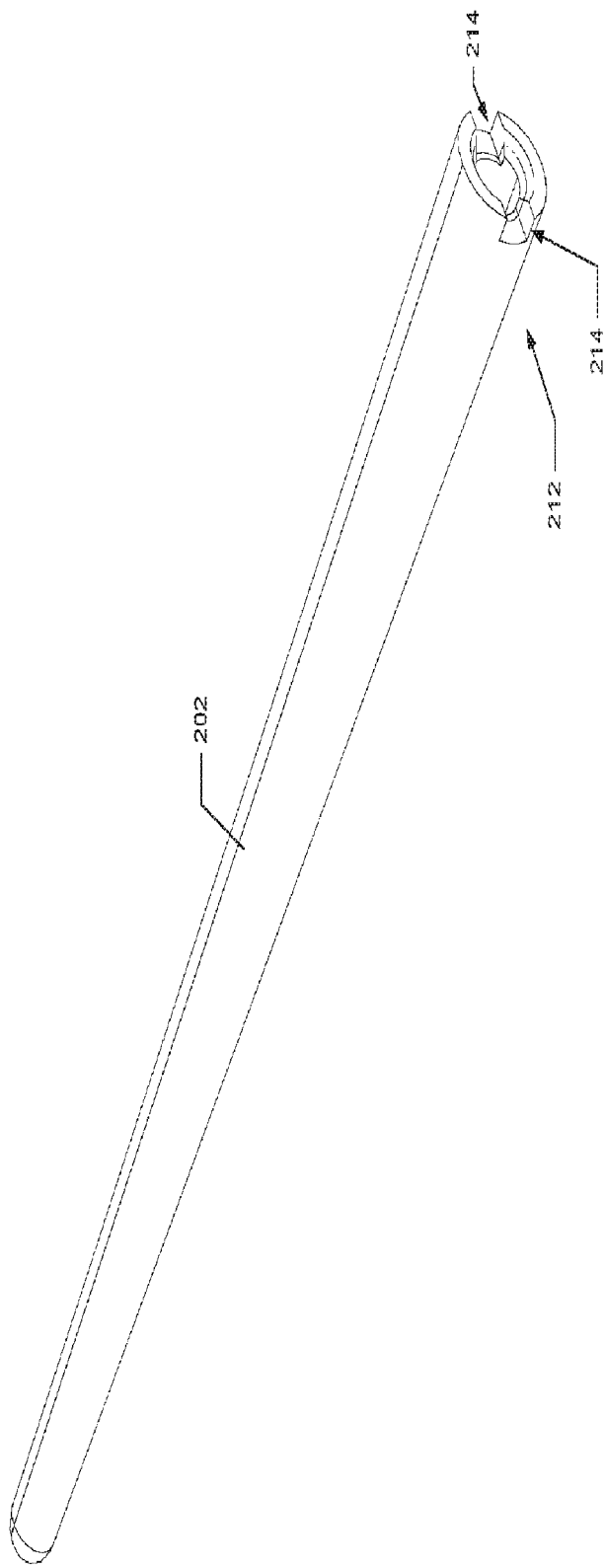
FIG. 17 is an isometric view of a stem of the ulnar component of the elbow implant device of FIG. 9.

In various embodiments, as shown in FIGS. 1-3, and 8, the ulnar component 200 is designed and configured for cemented fixation within the ulnar canal of a patient. The ulnar component 200 includes an ulnar stem 202 coupled to the ulnar bearing head 204 via an ulnar neck 206. In one aspect, the ulnar neck 206 extends at an acute angle "a" distally from the ulnar bearing head 204 in an anterior direction, as shown in FIG. 15. The ulnar neck 206 further includes a collar 208 from which a stem receptacle 210 extends in an anterior direction. In one embodiment, the stem receptacle 210 has a generally cylindrical or frusto-conical geometry. Alternatively, the stem receptacle may defined by other shapes or cross-sectional geometries. As shown in FIGS. 8 and 17, a proximal end 212 of the ulnar stem 202 may include mating features 214 such as projections, recesses, or both for securely mating with complimentary structures (not shown) within the stem receptacle 210. Alternately, the ulnar stem 202 may be engaged to the stem receptacle 210 through any suitable arrangement, including but not limited to a friction-fit or a threaded arrangement. In one aspect, the stem receptacle 210 defines a lumen 232 extending through the entire longitudinal length of the receptacle. As such, the receptacle lumen 232 may receive a tool opposite the stem 202 for using during implantation.

Figure 14:
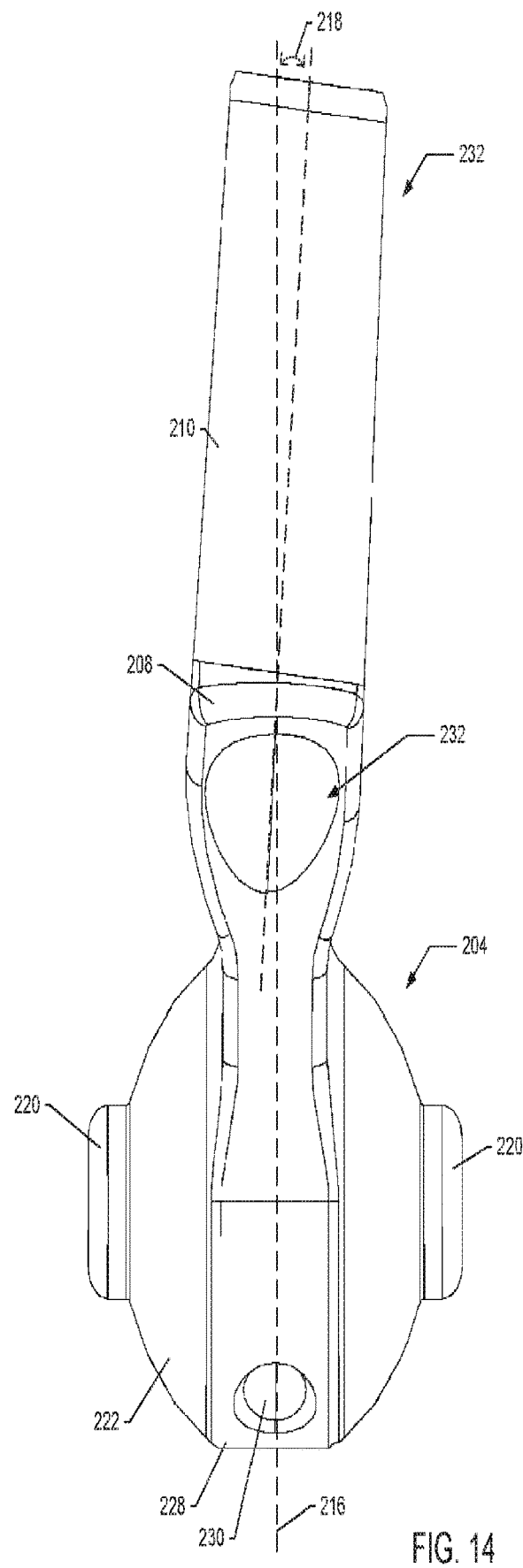
FIG. 14 is a rear perspective view of the bearing head, neck, and stem receptacle of the ulnar component of the elbow implant device of FIG. 13.
Figure 16:
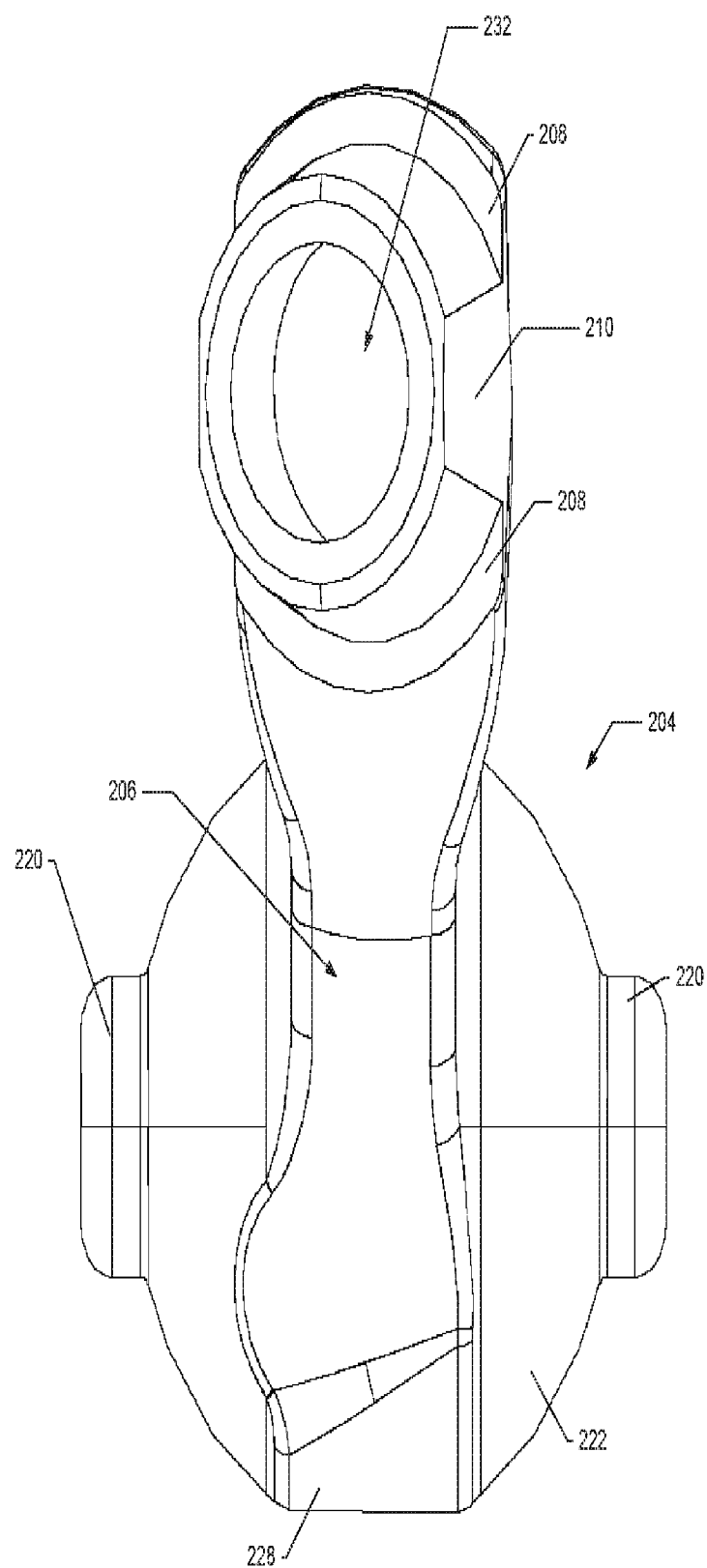
FIG. 16 is a bottom orthographic view of the bearing head, neck, and stem receptacle of the ulnar component of the elbow implant device of FIG. 13.

In yet another embodiment, the ulnar stem 202 and ulnar neck 206 may be fabricated in such a manner as to provide a unitary single-construct. In one aspect, as shown in FIGS. 14 and 16, the stem receptacle 210, and thus the ulnar stem 202 are angled laterally away from a longitudinal axis 216 of the ulnar bearing head 204, as generally indicated by 218. In various embodiment, the angle of deflection 218 is in a range between about 3.5 to 6.5 degrees. In one particular, embodiment, the angle of deflection 218 was approximately 5 degrees. In various aspects, the angle of deflection 218 replicates the natural carrying angle of the forearm. As such, the angle of deflection various in differing embodiments to account for anatomic differences and fit across male and female patients as well as differences between adult and pediatric patients.

The ulnar stem 202 is dimensioned for implantation within at least a portion of the proximal region of a patient's ulna. In various aspects, the ulnar stem 202 may be composed of one or more metallic or metallic alloy components. By way of example, the ulnar stem 202 may be composed of a single metal such as, but not limited to as cobalt-chrome (CoCr) alloy. In another aspect, the ulnar component 200 may be composed of one or more metal alloys. For example, the ulnar stem 202 may include a CoCr proximal portion, while the bearing head 204 and neck 206 are composed of titanium or a titanium alloy. Alternately, the entire ulnar component 200 may be composed of the same material.

The ulnar bearing head 204 is a spherical structure engaged to the ulnar neck 206. In various embodiments, the ulnar bearing head 204 may be integral with the ulnar neck 206. In other embodiments, the ulnar bearing head 204 may be formed separately from one or more other portions of the ulnar component 200.

Figure 13:
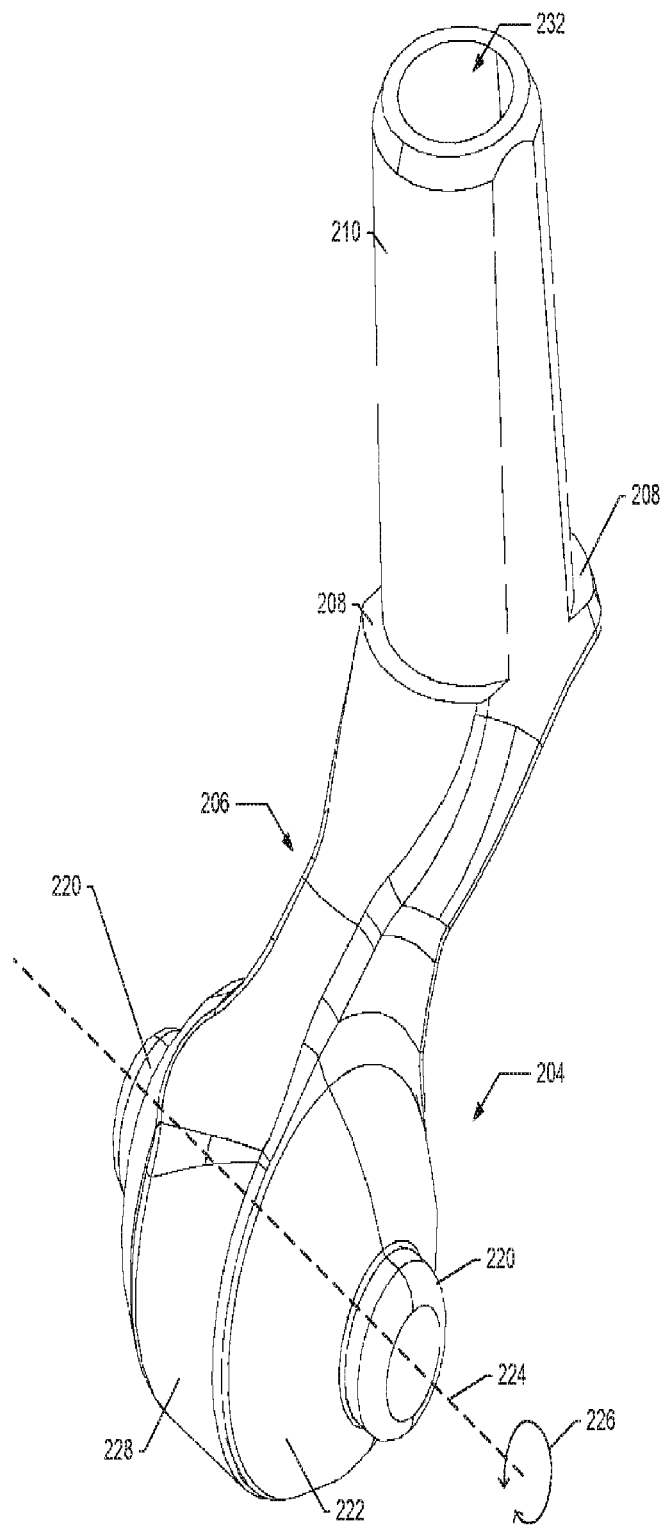
FIG. 13 is an isometric view of a bearing head, neck, and stem receptacle of the ulnar component of the elbow implant device of FIG. 9.

The ulnar bearing head 204 includes opposing ulnar bearing projections or ears 220. The ulnar bearing ears 220 extend away from the medial and lateral sides of the ulnar bearing surface 222 and are coaxial with a central transverse axis 224, as shown in FIGS. 14 and 16. In one aspect, the ulnar bearing ears 220 provide a transverse axis of rotation or articulation for the ulnar component 200, generally indicated as 224 in FIG. 13, when disposed within the humeral component 100.

The Articulation Bearing Liners

The elbow prosthesis 10 also includes one or more of the resilient articulation bearing inserts or liners 300, as shown in FIGS. 9, 18-20, and 26-28. In one embodiment, the elbow prosthesis 10 includes two articulation liners 300 that appear as mirror-images of each other and may be identified as a lateral articulation liner and a medial articulation liner. The liners 300 are composed of a polymer, including but not limited to polyethylene. In one aspect, the liners 300 aid the articulation of the ulnar component 200 by preventing metal-on-metal contact between the ulnar component and the humeral component 100. In another aspect, each of the liners 300 includes an exterior humeral interface surface 302 that remains fixed in a static orientation relative to the humeral component 100 following insertion and locking of the retention trap 400, as explained more fully below.

Figure 18:
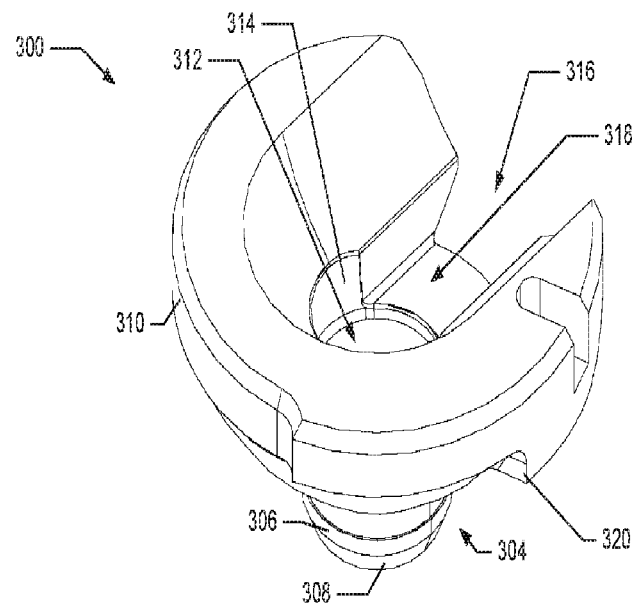
FIG. 18 is an isometric view of an articulation liner of the elbow implant device of FIG. 9.
Figure 19:
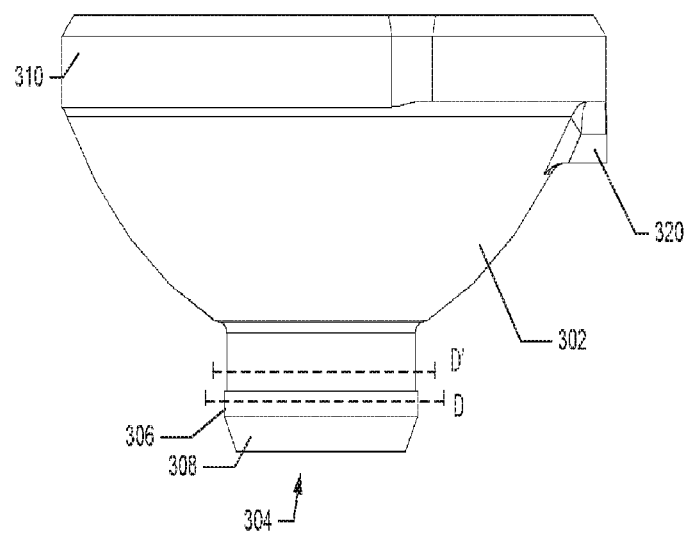
FIG. 19 is a front elevation view of the articulation liner of the elbow implant device of FIG. 18.

The exterior humeral interface surface 302 of the liners 300 has a generally hemispherical configuration similar to the interior surface 124 of each respective yoke branch 122. As such, the humeral interface surface 302 contacts the interior surface 124 of each respective yoke branch 122 of the humeral component 100. The exterior humeral interface surface 302 further defines a humeral interface stud 304 that extends away from the humeral interface surface. As shown in FIGS. 18 and 19, one embodiment of the bearing liner 300, the humeral interface stud 304 defines an annular collar 306 and frustoconical cap 308. The annular stud collar 306, preferably as an outer diameter "D" greater than an outer diameter "D" of the humeral interface stud 304, such that the interface stud may be inserted and removably retained within the bearing bore 130 of the yoke branch 122, as shown in FIG. 19. In various embodiments, the humeral interface stud 304 is retained in the bearing bore 130 using a detachable press-fit or snap lock arrangement. Alternately, in other embodiments, the humeral interface stud 304 and bearing bore 130 may be formed with complimentary threads to provide a threaded engagement.

Figure 20:
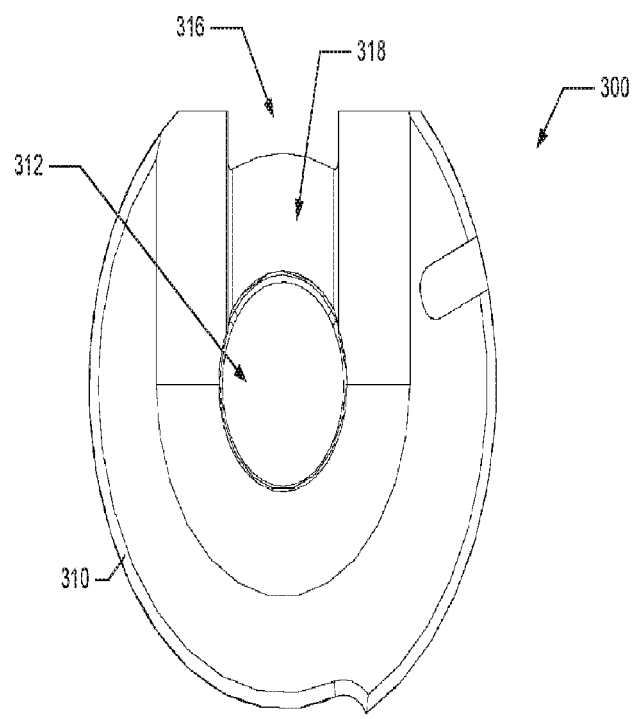
FIG. 20 is a top orthographic view of the articulation liner of the elbow implant device of FIG. 18.
Figure 28:
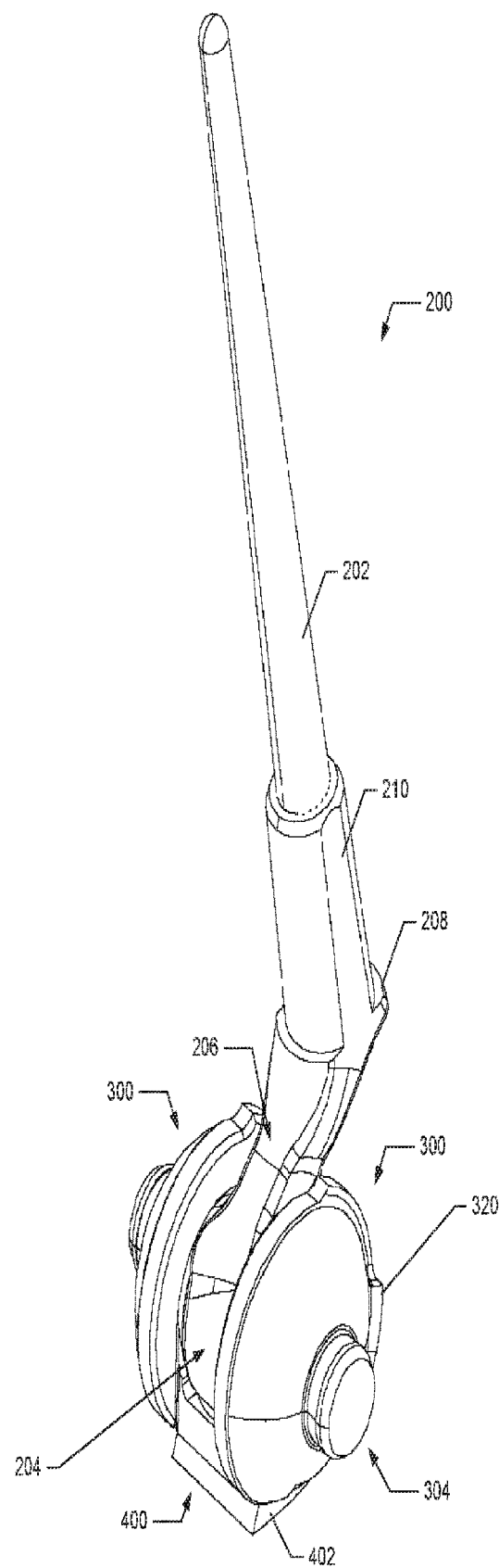
FIG. 28 is an isometric view of an ulnar component operatively engaged to a pair of articulation liners and a retention trap of the elbow implant device of FIG. 9.

The humeral interface stud 304 also defines an interior void 312, as shown in FIGS. 18 and 20 that is dimensioned to receive the bearing ears 220. The interior void surface 314 is composed of a polymer that permits articulation and rotation of the bearing ears 220 and therefore the ulnar component 200 once positioned within the bearing liners 300, as shown in FIG. 28.

Along the outer annular surface 310 of each of the bearing liners 300 a posterior trap opening 316 is in communication with a trap channel 318. The posterior trap opening 316 is defined along the outer circumference of the bearing liners 300. The posterior trap channel 318 is in communication with the opening 316 and disposed radially along an interior surface of the bearing liners 300. As shown in FIG. 7, when initially disposed with in the yoke branches 122, the posterior trap openings 316 of the liners 300 align with the trap shoulders 146 to form an aperture to receive the retention trap 400. Similarly, each posterior trap channel 318 also provides a conduit for receiving and guiding the ulnar bearing ears 220 into the desired position during assembly.

The outer annular surfaces 310 of the bearing liners 300 also include a locking flange 320. The locking flange 320 contacts the lock shoulder 148 of the slot 144 to lock the liners 300 into place once the liners are inserted and rotated into the hemispherical recesses 126. In particular, the liners 300 are engaged to the yoke branch 122 by inserting the humeral interface stud 304 into the bearing bore 130 and then rotating the liners into a locked position during assembly. This prevents the liners 300 and the ulnar component 200 from disassembling or dislocating once the liners are locked in place.

The Retention Trap

The retention trap 400, as shown in FIGS. 9 and 21-25 is a removable component that functions as a keystone to "lock" the ulnar component and the articulation bearing liners 300 within the humeral component 100. The retention trap 400 includes humeral component interface surfaces 402A-B, liner interface surfaces 404, and interior articulation surfaces 406 and ulnar bearing ear interface surfaces 408. In one aspect, the retention trap 400 is composed of a polymer, including but not limited to polyethylene.

By way of example and not limitation, in one embodiment, the humeral component interface surfaces 402A-B are static interfaces relative to the humeral component once fully assembled. In particular, humeral component interface surfaces 402A contact the interior edges 142 of the yoke branches 122, while the humeral component interface surfaces 402B contact the interior surface 124 of each respective yoke branch 122. In one aspect, the trap 400 is inserted through an opening defined by the trap shoulders 146, where the liner interface surfaces 404 translate past the trap shoulders. As such, once the retention trap 400 has been inserted into the humeral socket 106, engages the liners 300. During rotation to lock the liners 300 inside the humeral socket 106, the humeral component interface surfaces translate along the slot 144. After the liners 300 are locked in place, the trap remains in a static configuration, while the ulnar component 200 is able to articulate within the space bounded by the liners, the trap 400, and humeral socket 106. In this aspect, the retention trap 400 does not rotate or articulate with extension or flexion of the ulnar component.

Figure 21:
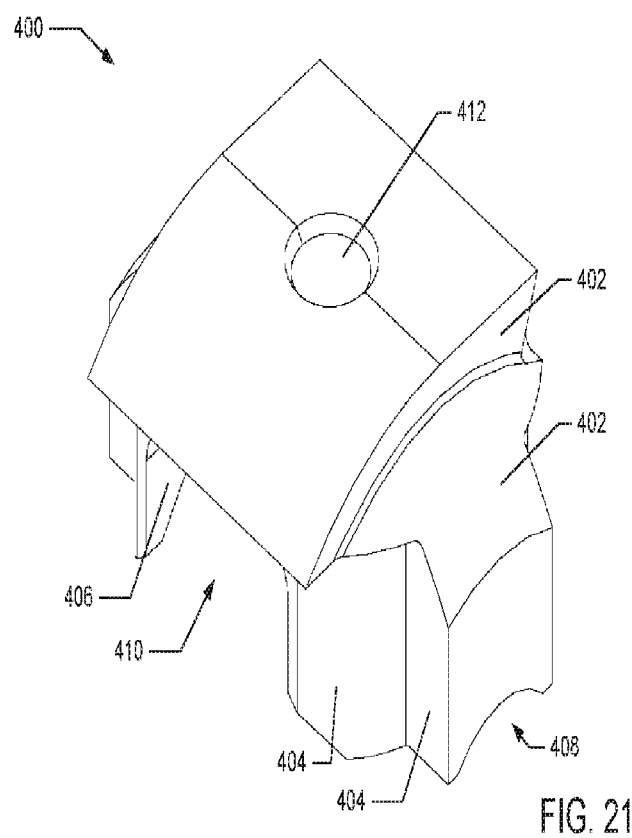
FIG. 21 is a top isometric view of a retention trap of the elbow implant device of FIG. 9.
Figure 22:
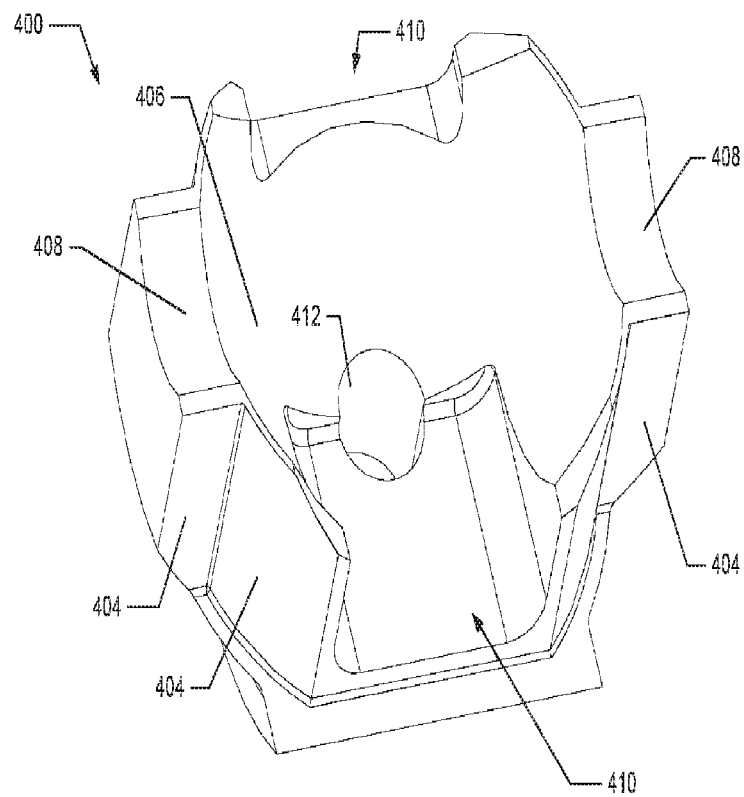
FIG. 22 is a bottom isometric view of the retention trap of the elbow implant device of FIG. 21.
Figure 23:
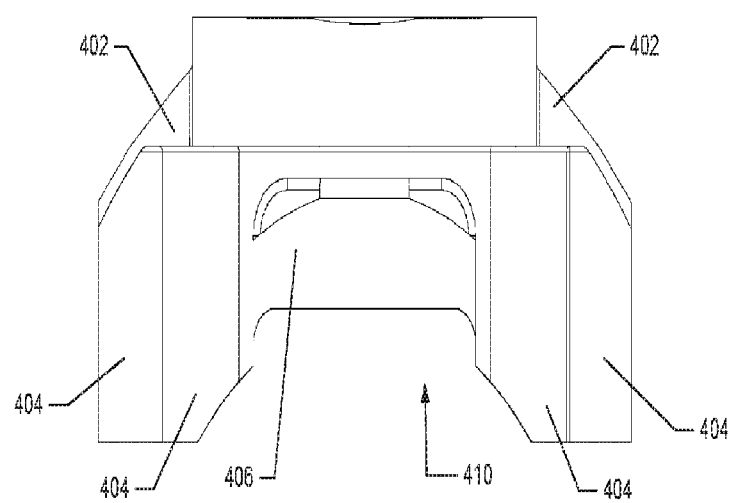
FIG. 23 is a front elevation view of the retention trap of the elbow implant device of FIG. 21.
Figure 24:
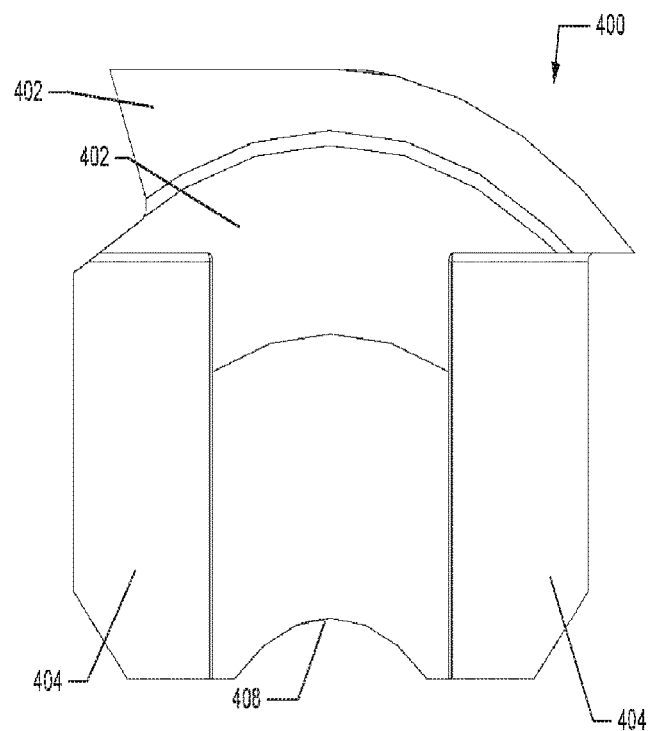
FIG. 24 is a side elevation view of the retention trap of the elbow implant device of FIG. 21.

The liner interface surfaces 404 of the trap also contact and engage the posterior trap channel 318 of the liner 300. As shown, the liner interface surfaces 404 are adjacent to the ulnar bearing ear interface surfaces 408, as shown in FIG. 21. The ulnar bearing ear interface surfaces 408 contact an exterior portion of the ulnar bearing ears 220 that are disposed with the stud interior void 312. As shown in FIGS. 21, 22 and 24, the bearing ear interface surfaces 408 are generally concave and have a radius of curvature substantially similar to that of the ulnar bearing ears 220.

Figure 25:
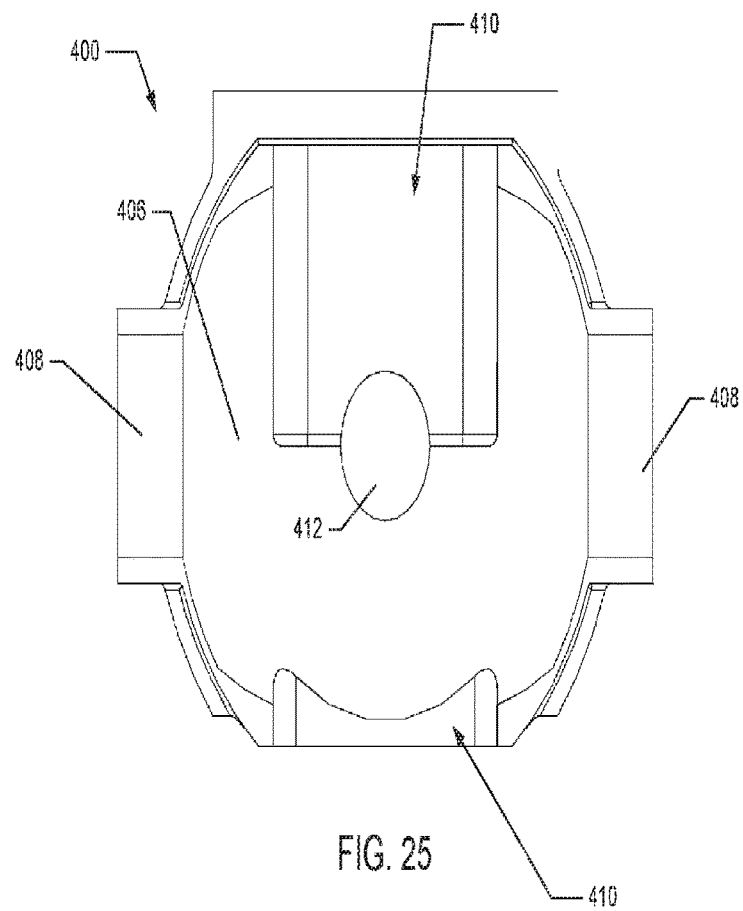
FIG. 25 is a bottom orthographic view of the retention trap of the elbow implant device of FIG. 21.

The interior articulation surfaces 406 are generally concave and contact the ulnar component 200 which articulates against them during flexion and extension of the assembled prosthetic device 10. As shown in FIGS. 2, 22 and 25, the interior articulation surfaces 406 may further define an extension channel 410 that permits full extension of the ulnar component 200 when it is positioned within the humeral component. During assembly, the trap 400 and liners 300 are rotated relative to the humeral component 100 until the liners "snap" into place. Once this occurs, the prosthetic device 10 is considered locked.

The retention trap 400 also includes a tool bore 412 that extends from the outer surface of the trap to the interior articulation surface 406, as shown in FIGS. 21-22 and 32-36. As explained, more fully below, the tool bore 412 is dimensioned to receive a tool (not shown) that extends through the retention trap 400 and engages the ulnar component 200 in an ulnar bore 230 shown in FIG. 14. A tool inserted through the tool bore 412 provides leverage to rotate the trap 400 and liners 300 during installation or removal of the device 10.

Figure 29:
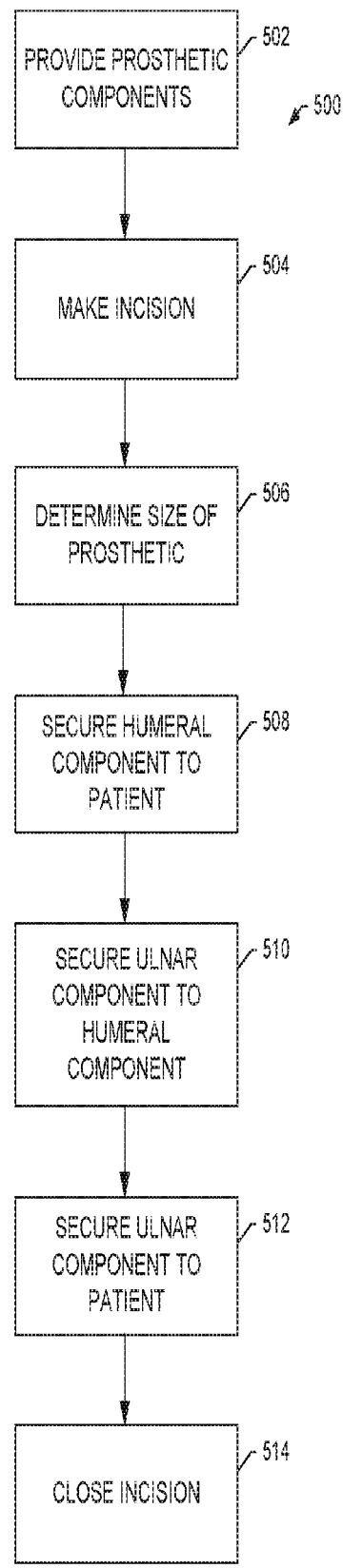
FIG. 29 is a flow chart of a method to implant the elbow implant device of FIG. 1, according to one embodiment.

The present disclosure also relates to various methods for implanting, assembling, and using the elbow prosthetic device 10. FIG. 29 is a flow chart depicting one embodiment of a method 500 for implanting and using any embodiment of the elbow prosthesis 10, as described above. At 502, an unassembled prosthetic device, such as the prosthetic device 10 is provided. In one aspect, the unassembled device includes the humeral component 100, the ulnar component 200, the bearing liners 300, and the retention trap 400. After proper patient preparation and sterilization, as understood by one having ordinary skill in the art, an incision is made in a desired arm of patient at 504 to expose the implantation site. In one aspect, the condition of the patient's ulna and humerus are accessed to determine the amount of hard and/or soft tissue that must be resected. The ulna and humerus may undergo additional preparation to prepare the bones for receiving the implants. This preparation includes any number of steps readily understood by one having ordinary skill in the art. For example, in one aspect, a distal end of the humerus may be resected and additional bone fragments may be removed to expose the distal end of the humerus.

After making the incision and, optionally, visually inspecting the patient, the proper size for each of the components of the device 10 is determined at 506. This determination may be made using diagnostic imaging or other sizing determinations, including but not limited to visual comparisons. In one aspect, a size determination for each component of the device 10 may include temporarily implanting various sizes of the humeral component 100 and the ulnar component 200, while assessing such factors as the soft tissue balance, the range of motion, joint spacing, and stability, among others.

Figure 30:
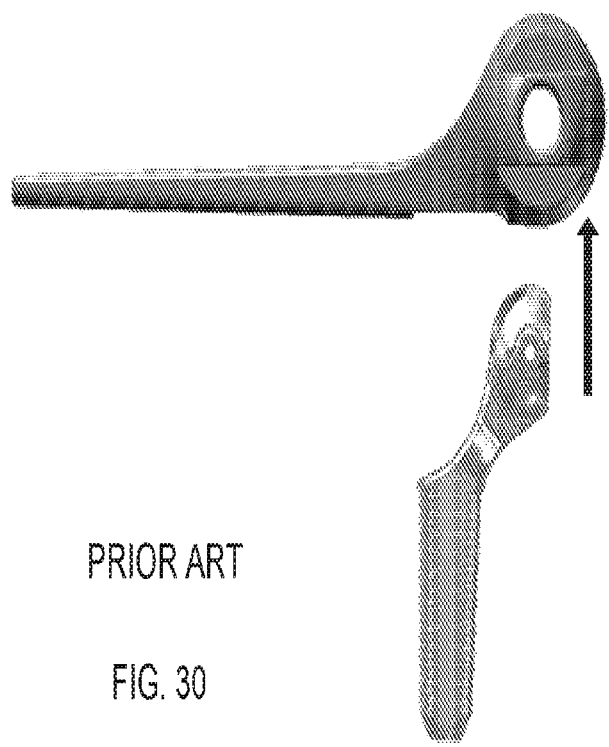
FIG. 30 is an illustration of an existing elbow arthoplasty device that must be assembled in a single configuration.
Figure 31:
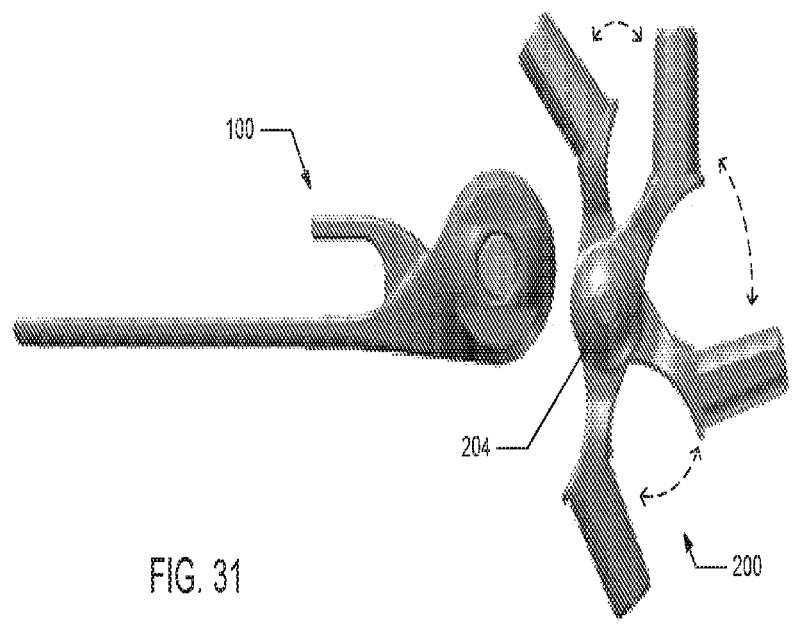
FIG. 31 is an illustration of one embodiment of the present elbow arthoplasty device that may be assembled in a number of configurations.
Figure 32:
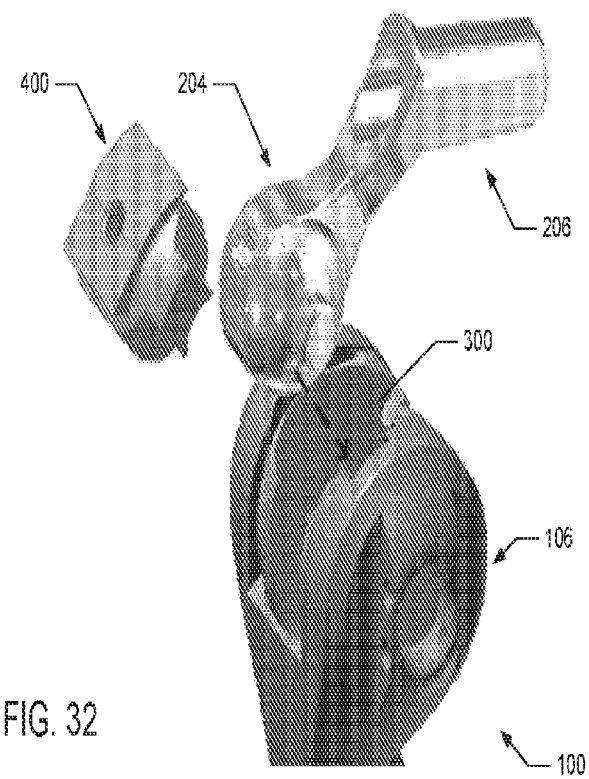
FIG. 32 is a rear isometric view of a step of a method to implant the elbow implant device according to one embodiment.
Figure 33:
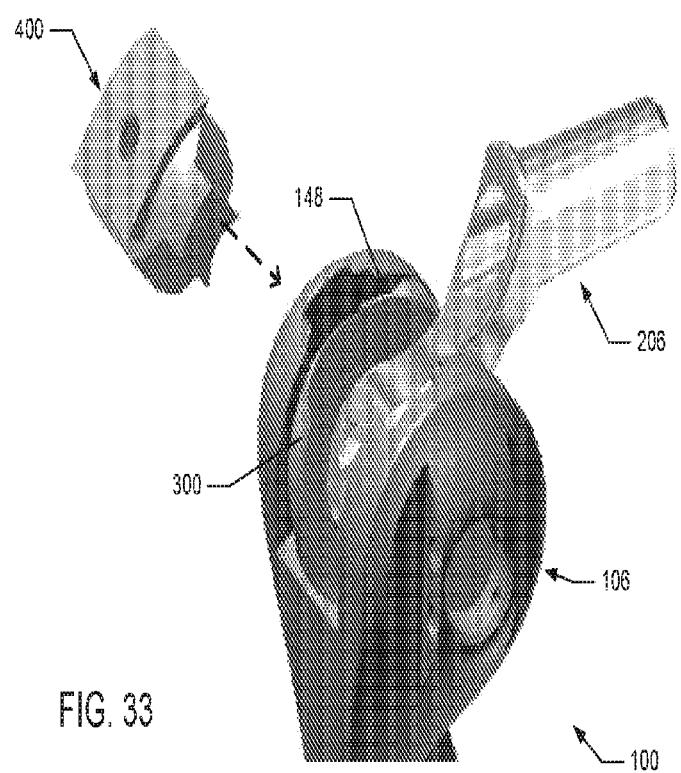
FIG. 33 is a rear isometric view of a step of a method to implant the elbow implant device according to one embodiment.
Figure 34:
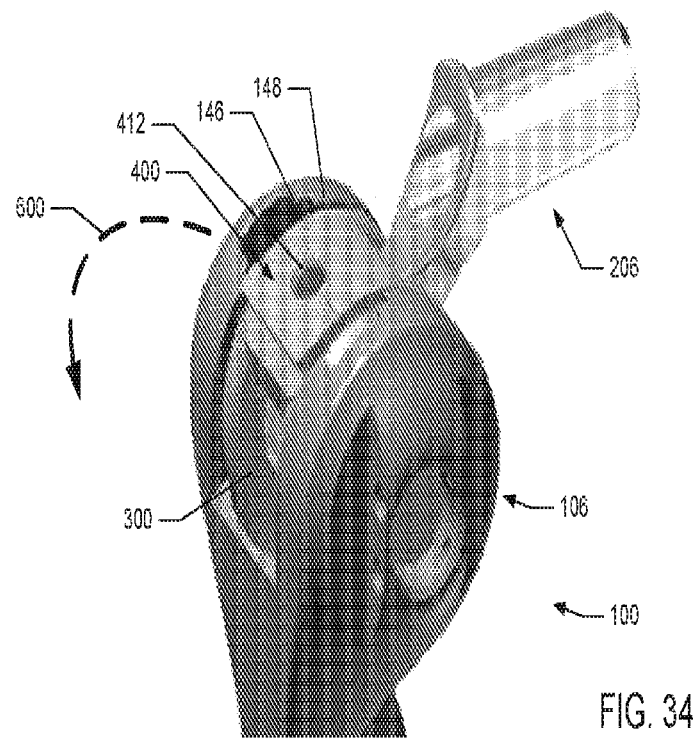
FIG. 34 is a rear isometric view of a step of a method to implant the elbow implant device according to one embodiment.
Figure 35:
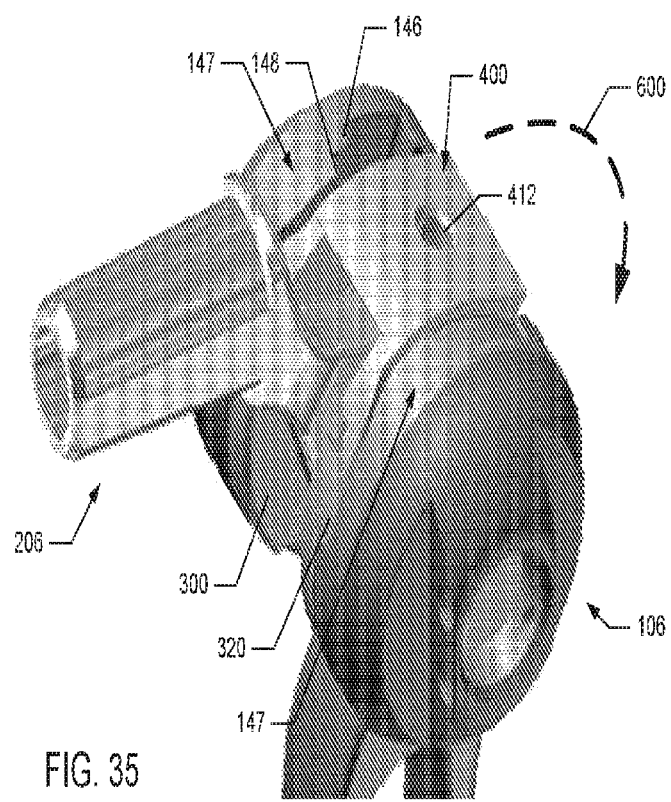
FIG. 35 is a front isometric view of the step of a method to implant the elbow implant device shown in FIG. 34, according to one embodiment.
Figure 36:
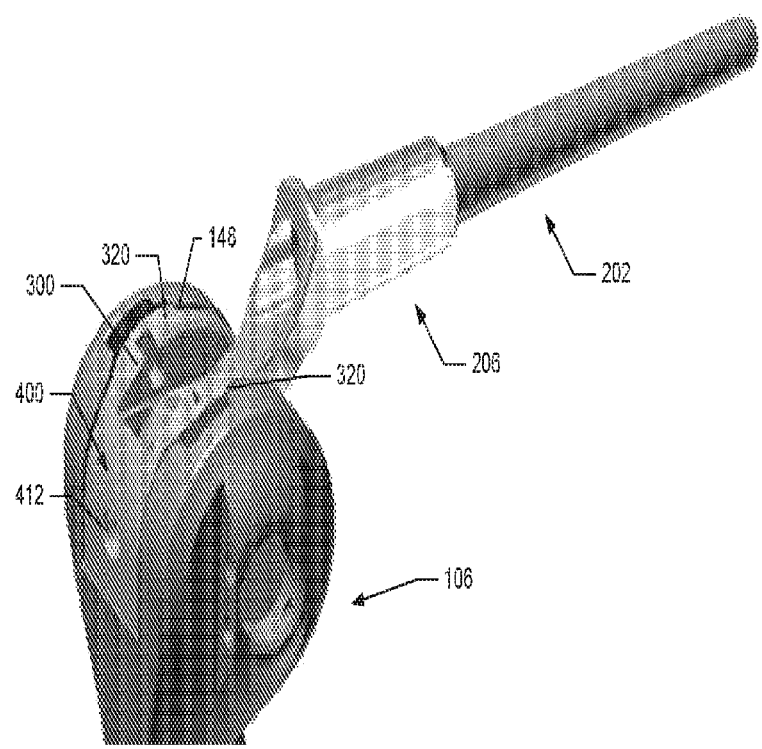
FIG. 36 is a rear isometric view of one step of a method to implant the elbow implant device according to one embodiment.

At 508 and 510, the humeral component 100 is secured to the humerus of the patient and the ulnar component 200 is attached to the humeral component, respectively. In one aspect, attaching the ulnar component 200 to the humeral component 100 may also include rotatably coupling the ulnar component to the humeral component. In another aspect, when attaching the ulnar component to the humeral component 100, one or more bearing liner 300 is secured to the inner surface of the humeral socket 106. In yet another aspect, the ulnar component 200 is rotated from ninety degrees of hyperextension with respect to the humeral component 100 and rotating the ulnar component from extension into flexion during assembly. As shown in FIGS. 30-31, one advantageous feature of the ulnar component 200 is that the fully spherical bearing head 204 may be inserted into the humeral socket 206 in any of a number of orientations.

In one aspect, The ulnar component 200 is locked and retained within the humeral component 100 using the bearing liners 300 in combination with the retention trap 400. For example in this aspect, as shown in FIGS. 32-36, the ulnar component 200, or at least the bearing head and neck portion thereof, is inserted into the humeral socket 106 after placement of the bearing liners 300. The retention trap is then inserted into the opening defined by the trap shoulders 146. The retention trap and bearing liners 300 are then rotated about the ulnar component 200 in a posterior direction, generally indicated as 600, away from the humeral flange 104. This rotation causes the resilient outer annular surfaces 310 and the locking flange 320 in particular, to be compressed or flexed inwards towards the ulnar neck 206 as they contact and traverse the narrowed region 149 of the slot 144. Once the locking flange 320 of each liner 300 has traversed the narrowed region 149, the resilient annular surfaces flex outward, where the locking flange engages the lock should 148 to prevent retrograde rotation of the liners. Simultaneous with the liner 300 rotation, the retention trap 400 is also rotated such that the humeral component interface surfaces 402A slide along the interior edges 142 of the yoke branches 122, while the humeral component interface surfaces 402B contact and slide the interior surface 124.

Figure 26:
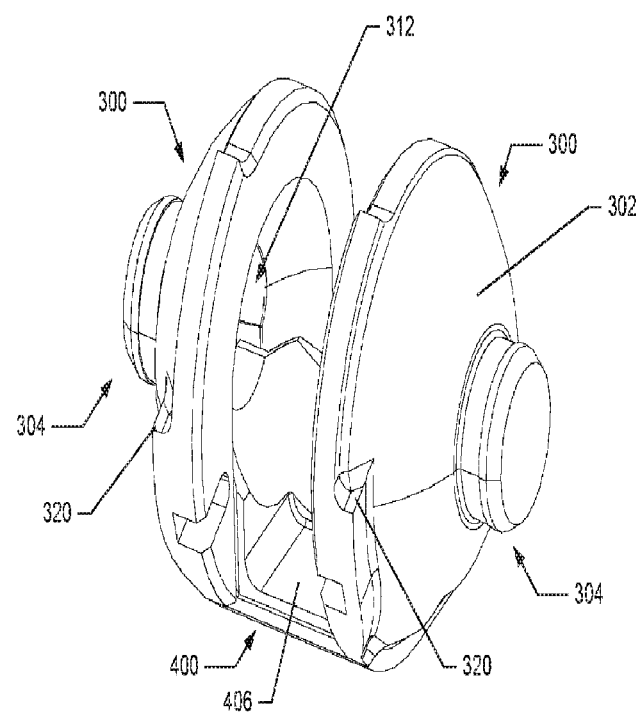
FIG. 26 is an isometric view of a pair of articulation liners engaged to a retention trap of the elbow implant device of FIG. 9.
Figure 27:
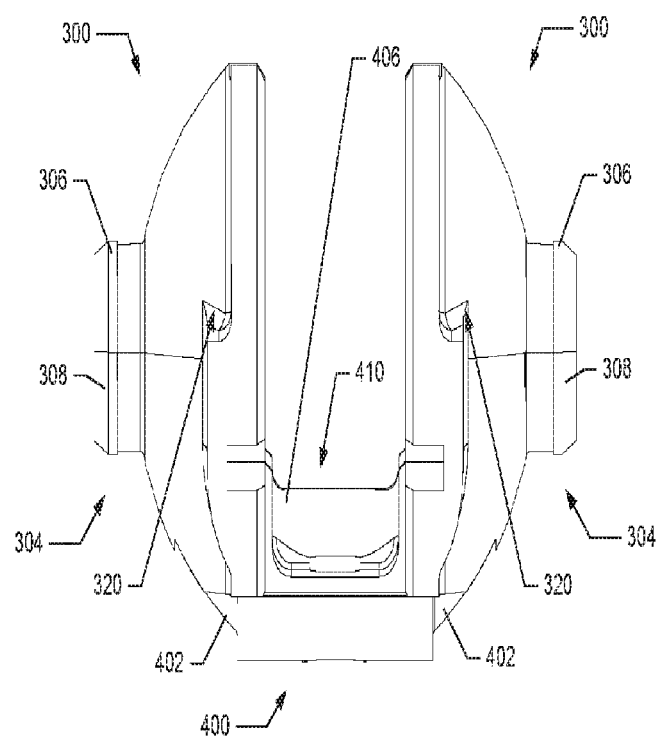
FIG. 27 is a rear perspective view of a pair of articulation liners engaged to a retention trap of the elbow implant device of FIG. 26.

As the retention trap 400 is fittingly engaged to the liners as shown in FIGS. 26-28, it is also prevented from retrograde rotation. Additionally, the humeral component interface surfaces 402B prevent the retention trap from translating in a posterior direction out of the slot 144. Both the retention trap 400 and liners 300 are therefore immobilized within the humeral socket 106, which therefore prevents the unintentional removal of the ulnar bearing 204 from the humeral socket. FIGS. 32-35 illustrate an embodiment of the method 500, where a portion of the ulnar component 200 such as the ulnar bearing 204 and the ulnar neck 206 are be engaged and retained in the humeral socket 206 before the ulnar stem 202 is engaged to the neck. In other embodiments, the liners 300 and retention trap 400 may be rotated and/or locked after the stem 2002 is engaged to the ulnar neck 206.

At 512, the ulnar component 200 is secured to the ulna of the patient. In other embodiments, the ulnar component 200 is secured in the ulna of the patient prior to attaching the ulnar component to the humeral component 100. In one alternate embodiment, after securing the ulnar component 200 to the ulna, the ulnar component is then engaged to the humeral component 100.

At 514, the incision in the patient is closed. According to other embodiments, prior to closing the incision, a guiding system including an insertion tool may be used for inserting at least one fixation device into the stem of the ulnar component prior to implantation. Additionally, soft tissue structures proximal the elbow prosthesis 10 may be balanced and attached to the prosthesis using sutures or other suitable connecting components. Moreover, the functionality of the implanted elbow prosthesis 10 may be assessed before closing the incision, after closing the incision, or both.

In various other embodiments, the order of the steps for affixing the device 10 to the patient the device may be varied; however to securely engage the ulnar component 200 to the humeral component 100, the liners 300 are positioned with humeral socket 106 prior to inserting the bearing head 204, regardless of orientation, as shown in FIG. 31.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method for implanting an elbow prosthesis in a patient, the method comprising:
   obtaining the elbow prosthesis, the elbow prosthesis including:
      an ulnar component including a bearing end and an ulnar stem, wherein the ulnar stem extends away from the bearing end,
      a humeral component including a holder end and a humeral stem, wherein the humeral stem extends away from the holder end, and
      at least one bearing liner coupled to the holder end, wherein the bearing end is configured to be coupled within the holder end to articulate against the at least one bearing liner;
   making an incision in the patient to thereby expose an implantation site for the elbow prosthesis;
   determining a proper size for the ulnar component and for the humeral component;
   preparing an ulna and a humerus of the patient;
   securing the humeral component in the humerus of the patient;
   securing the ulnar component in the ulna of the patient;
   attaching the ulnar component to the humeral component; and
   closing the incision in the patient, wherein the elbow prosthesis further includes a retention trap, and wherein attaching the ulnar component to the humeral component includes rotating the retention trap relative to the humeral component thereby locking the ulnar component within the humeral component.

2. The method of claim 1, further comprising assessing the condition of the ulna and the humerus to determine a degree of hard and soft tissue resection.

3. The method of claim 1, wherein preparing the humerus of the patient includes resecting a distal end of the humerus and removing fracture fragments to expose the distal end of the humerus.

4. The method of claim 1, wherein determining the proper size for the ulnar component and for the humeral component includes:
   temporarily implanting two or more different sizes of the ulnar component or the humeral component; and
   assessing at least one of soft tissue balance, range of motion, joint spacing, and stability between the two or more different sizes of the ulnar component or the humeral component.

5. The method of claim 1, wherein attaching the ulnar component to the humeral component includes rotatably coupling the ulnar component to the humeral component.

6. The method of claim 1, wherein attaching the ulnar component to the humeral component includes securing the at least one bearing liner to an inner surface of the holder end.

7. The method of claim 1, wherein the ulnar component is attached to the humeral component prior to securing the ulnar component in the ulna of the patient.

8. The method of claim 7, wherein the ulnar component is attached to the humeral component prior to securing the humeral component in the humerus of the patient.

9. The method of claim 1, wherein the ulnar component is secured in the ulna of the patient and the humeral component is secured in the humerus of the patient prior to attaching the ulnar component to the humeral component.

10. The method of claim 1, further comprising attaching surrounding soft tissue structures to the elbow prosthesis.

11. The method of claim 1, wherein the retention trap includes a bore, and wherein the method includes inserting an instrument into the bore and rotating the retention trap via the instrument.

12. A method for implanting an elbow prosthesis in a patient, the method comprising:
   obtaining the elbow prosthesis, the elbow prosthesis including:
      an ulnar component including a bearing end and an ulnar stem, wherein the ulnar stem extends in a distal direction from the bearing end,
      a humeral component including a holder end and a humeral stem, wherein the humeral stem extends in a proximal direction from the holder end, and
      a coupling mechanism, the coupling mechanism including at least one bearing liner, the bearing end, and the holder end,
      wherein the at least one bearing liner is positioned within the holder end and the bearing end is configured to be rotatably coupled within the holder end and articulate against the at least one bearing liner;
   making an incision in the patient to thereby expose an implantation site for the elbow prosthesis;
   determining a proper size for the ulnar component and for the humeral component;
   preparing an ulna and a humerus of the patient;
   securing the humeral component into the humerus of the patient;
   rotatably coupling the ulnar component to the humeral component;
   securing the ulnar component in the ulna of the patient; and
   closing the incision in the patient,
   wherein the elbow prosthesis further includes a retention trap, and wherein rotatably coupling the ulnar component to the humeral component includes:
   inserting the bearing end of the ulnar component into the holder end of the humeral component adjacent to the at least one bearing liner;
   inserting the retention trap into the holder end;
   securing the at least one bearing liner to an inner surface of the holder end by rotating the at least one bearing liner within the humeral component to engage a locking flange of the at least one bearing liner with the a locking shoulder of the humeral component; and
   rotating the retention trap and the at least one bearing liner relative to the humeral component to lock the retention trap and the at least one bearing liner to the humeral component.

13. The method of claim 12, wherein rotatably coupling the ulnar component to the humeral component includes attaching the ulnar component to the humeral component and rotating the ulnar component from hyperextension with respect to the humeral component into flexion.

14. The method of claim 13, wherein the attached ulnar component is rotated from ninety degrees of hyperextension.

15. The method of claim 12, wherein the at least one bearing liner and the retention trap are prevented from further rotation upon locking the retention trap and the at least one bearing liner to the humeral component.

16. The method of claim 12, wherein the retention trap is operatively engaged to the at least one bearing liner during rotation of the retention trap and the at least one bearing liner.

17. The method of claim 12, wherein the ulnar component is secured in the ulna of the patient subsequent to the humeral component being secured in the humerus of the patient and the ulnar component being rotatably coupled to the humeral component.

18. The method of claim 12, wherein the holder end of the humeral component includes a pair of opposing yoke branches each defining a respective yoke slot, wherein each respective yoke slot includes a respective locking shoulder, and wherein each respective locking shoulder operatively engages the at least one articulation liner to prevent rotation of the at least one articulation liner after rotatably coupling the ulnar component to the humeral component.

* * * * *